United States Patent
Watanabe et al.

(10) Patent No.: US 6,967,781 B2
(45) Date of Patent: Nov. 22, 2005

(54) IMAGE DISPLAY APPARATUS FOR DISPLAYING IMAGE IN VARIABLE DIRECTION RELATIVE TO VIEWER

(75) Inventors: Mitsuyoshi Watanabe, Hashima (JP); Shoji Yamada, Kounan (JP)

(73) Assignee: Brother Kogyo Kabushiki Kaisha, Nagoya (JP)

( * ) Notice: Subject to any disclaimer, the term of this patent is extended or adjusted under 35 U.S.C. 154(b) by 0 days.

(21) Appl. No.: 10/716,525

(22) Filed: Nov. 20, 2003

(65) Prior Publication Data

US 2004/0109135 A1 Jun. 10, 2004

(30) Foreign Application Priority Data

Nov. 29, 2002 (JP) ............................. 2002-348266

(51) Int. Cl.⁷ ........................................... G02B 27/14
(52) U.S. Cl. ..................................... 359/630; 359/726
(58) Field of Search ................................ 359/629–633, 359/726–727, 730, 13, 197, 212; 351/209–210; 345/7–9, 345/32; 348/53, 744–745, 750; 600/558

(56) References Cited

U.S. PATENT DOCUMENTS

| | | | | |
|---|---|---|---|---|
| 5,489,950 A | * | 2/1996 | Masuda | 348/744 |
| 6,352,344 B2 | * | 3/2002 | Tidwell | 351/209 |
| 6,639,570 B2 | * | 10/2003 | Furness et al. | 345/8 |

FOREIGN PATENT DOCUMENTS

JP B2 2874208 1/1999

* cited by examiner

*Primary Examiner*—Jordan M. Schwartz
(74) *Attorney, Agent, or Firm*—Oliff & Berridge PLC

(57) ABSTRACT

An apparatus for introducing a light beam into a pupil of an eye of a viewer, to thereby project an image onto a retina of the eye is disclosed, in which a light beam generator generates and outputs a light beam corresponding to the image, a scanning device scans the light beam output by the light beam generator, a guiding device guides the light beam scanned by the scanning device toward the pupil, and an angle modifying device modifies a pupil incident angle at which a center line of a scanning angle of the scanning device enters the pupil.

18 Claims, 14 Drawing Sheets

IMAGE DISPLAY APPARATUS FOR DISPLAYING IMAGE IN VARIABLE DIRECTION RELATIVE TO VIEWER

This application is based on Japanese Patent Application No. 2002-348266 filed Nov. 29, 2002, the content of which is incorporated hereinto by reference.

CROSS-REFERENCE TO RELATED APPLICATIONS

Not applicable.

BACKGROUND OF THE INVENTION

1. Field of the Invention

The present invention relates in general to an image display apparatus for introducing a light beam into the pupil of a viewer, and for projecting an image onto the retina of the viewer with the light beam introduced, for thereby permitting the viewer to view a virtual image in front of the pupil.

2. Description of the Related Art

Recently, various image display apparatuses have been devised, each of which introduces a light beam into the pupil of a viewer, and which projects an image onto the retina of the viewer with the light beam introduced, for thereby permitting the viewer to view a virtual image in front of the pupil. They are each referred to as "Retinal Scanning Display."

Japanese Patent No. 2874208 discloses an example of a conventional image display apparatus of the type described above. This example is an apparatus with a plurality of components thereof for displaying an image for a viewer.

The above example of the conventional image display apparatus is constructed to include: (a) a light source for emitting a light beam and permitting modulation of the intensity of the emitted light beam; (b) a wave-front-curvature modulator for modulating the curvature of a wave front of the light beam emitted from the light source; (c) a deflector for deflecting the light beam; (d) an optical path element for letting the light beam propagate between the aforementioned plurality of components; and (e) an optical system for letting the light beam enter the viewer's pupil.

The optical system mentioned above is designed to cause the light beam to enter the pupil, after the light beam is modulated by the corresponding components with respect to the angle of the light beam incident to the pupil; and with respect to the curvature of the wave front and the intensity of the light beam.

Furthermore, the thus exemplified image display apparatus is used such that the light beam is scanned by the above deflector, and such that the scanned light beam enters the retina of the viewer's eye, resulting in a direct projection of an image onto the retina.

Eventually, the exemplified image display apparatus allows the viewer to view a virtual image in front of the pupil in the direction of a line defined by extending back the light beam entering the pupil. It is therefore followed that the direction of the light beam entering the pupil determines a display direction in which a virtual image is displayed relative to the viewer.

BRIEF SUMMARY OF THE INVENTION

Having studied the above kind of image display apparatus, the present inventor has reached the following findings:

For example, there is not always a consistency between display directions in which different viewers desire to perceive virtual images, due to differences between the different viewers in terms of preferences, inclinations and so on.

In addition, even the same viewer may desire to vary the display direction of a virtual image depending upon the purposes of viewing the virtual image. For instance, where the image display apparatus is of a see-through type allowing a viewer to perceive a virtual image along with the outside real world view, the viewer may desire to perceive the virtual image as a primary image and the outside real world view as a reference image, or conversely, the viewer may desire to perceive the outside real world view as a primary image and the virtual image as a reference image.

Therefore, an enhanced easiness-to-use of the above type of image display apparatus would be provided by enabling the image display apparatus to modify the above display direction of a virtual image. On the other hand, the above display direction of a virtual image is changed by modifying an incident angle at which a scanning center line enters the pupil, wherein the scanning center line is the center line of the angular range within which the light beam is scanned to display a virtual image.

It is therefore an object of the present invention to provide, based on the above-described findings, an image display apparatus capable of changing a display direction in which a virtual image is displayed relative to a viewer, with an enhanced easiness-to-use thereof.

In view of the above, the present invention provides an apparatus for displaying an image in a variable direction relative to a viewer. More specifically, the present invention provides an apparatus for generating and outputting a light beam corresponding to the image, scanning the light beam output, directing the light beam scanned toward a pupil of the viewer, and modifying a pupil incident angle at which a center line of a scanning angle of the light beam enters the pupil.

The change in the above incident angle results in the change in the direction in which the viewer perceives a virtual image, wherein the direction corresponds to the direction of the display position of the virtual image relative to the viewer.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
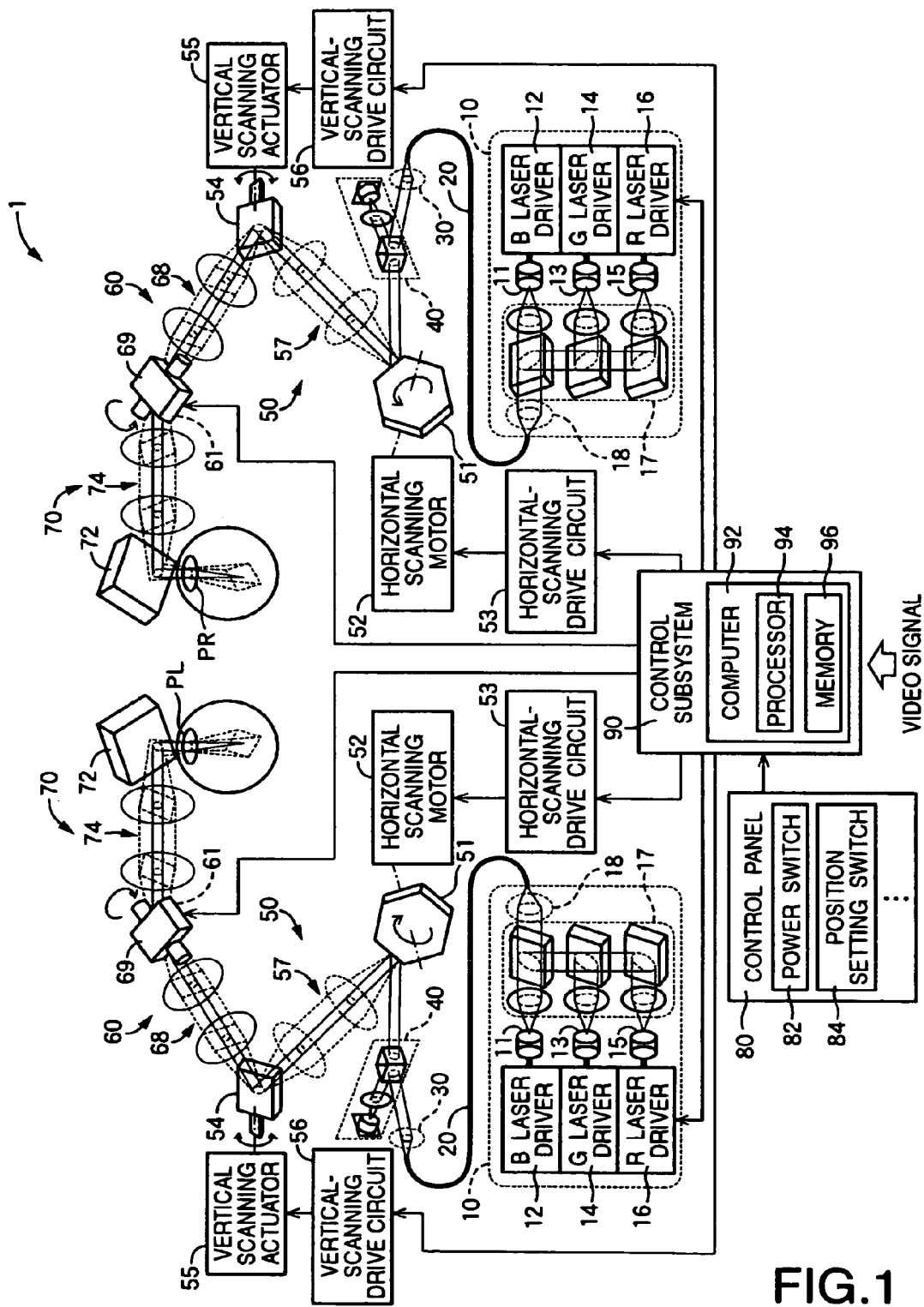
FIG. 1 is a schematic view illustrating an image display apparatus according to a first embodiment of the invention.

The object mentioned above may be achieved according to any one of the following modes of this invention.

These modes will be stated below such that these modes are sectioned and numbered, and such that these modes depend upon the other mode or modes, where appropriate. This is for a better understanding of some of a plurality of technological features and a plurality of combinations thereof disclosed in this description, and does not mean that the scope of these features and combinations is interpreted to be limited to the scope of the following modes of this invention.

That is to say, it should be interpreted that it is allowable to select the technological features which are stated in this description but which are not stated in the following modes, as the technological features of this invention.

Furthermore, stating each one of the selected modes of the invention in such a dependent form as to depend from the other mode or modes does not exclude a possibility of the technological features in a dependent-form mode to become independent of those in the corresponding depended mode or modes and to be removed therefrom. It should be interpreted that the technological features in a dependent-form mode is allowed to become independent according to the nature of the corresponding technological features, where appropriate.

(1) An apparatus for introducing a light beam into a pupil of an eye of a viewer, to thereby project an image onto a retina of the eye, the apparatus comprising:

a light beam generator for generating and outputting a light beam corresponding to the image;

a scanning device for scanning the light beam output by the light beam generator;

a guiding device for guiding the light beam scanned by the scanning device toward the pupil; and an angle modifying device for modifying a pupil incident angle at which a center line of a scanning angle of the scanning device enters the pupil.

In the apparatus according to the above mode (1), firstly, the light-beam generator generates and outputs the light beam corresponding to the image. Secondly, the scanning device scans the light beam output by the light-beam generator. Eventually, the guiding device directs the light beam scanned by the scanning device toward the viewer's pupil.

In the apparatus according to the above mode (1), additionally, the angle modifying device modifies the pupil incident angle, which is defined as an angle at which the center line of the scanning angle of the scanning device enters the pupil.

Therefore, the apparatus according to the above mode (1) allows a change in the incident angle at which the scanned light beam enters the pupil, and resultantly allows a change in the direction in which the viewer perceives a virtual image, namely, the direction of the display position of a virtual image relative to the viewer.

(2) The apparatus according to the mode (1), wherein the angle modifying device is disposed at a position within a path extending from the scanning device to the guiding device, the position having an optical conjugate relationship with a position of the pupil.

In the apparatus according to the above mode (2), the angle modifying device set forth in the mode (1) is located so as to have an optical conjugate relationship with the position of the viewer's pupil (the position corresponding to the pupil).

Therefore, the apparatus according to the above mode (2) causes the light beam from the scanning device into the pupil via the guiding device to be focused or converged at a fixed position (hereinafter referred to as "focus position") in the pupil, regardless of a possible change in the aforementioned pupil incident angle.

For the reason, the apparatus according to the above mode (2) eliminates a possibility of the above-defined focus position to move away from the position corresponding to the pupil due to a large change in the direction of the display position of a virtual image.

As a result, the apparatus according to the above mode (2) eliminates an inaccurate perception of a virtual image by the viewer and an incapability of the viewer to perceive a virtual image because of a change in the direction of the display position of a virtual image, and eventually results in a capability to extensively modify the direction of the display position of a virtual image.

The "guiding device" set forth in the above mode (2) preferably includes, in order to establish an optical conjugate relationship between a plurality of optical constituents of the apparatus, an optical system for converging a light beam, for example.

(3) The apparatus according to the mode (1) or (2), wherein the angle modifying device includes:

a first modifier for modifying the pupil incident angle with respect to a first modifying direction; and a second modifier for modifying the pupil incident angle with respect to a second modifying direction intersecting the first modifying direction.

The apparatus according to the above mode (3) allows a modification of the aforementioned pupil incident angle with respect to two directions, and as a result, allows a change in the direction of the display position of a virtual image relative to the viewer in two dimensions.

(4) The apparatus according to any one of the modes (1) to (3), wherein the scanning device includes:

a first scanner for scanning the light beam in a first scanning direction;

a second scanner for scanning the light beam scanned by the first scanner in a second direction intersecting the first scanning direction; and a relay optical system for introducing the light beam from the first scanner to the second scanner, such that the first scanner and the second scanner have an optical conjugate relationship therebetween.

The apparatus according to the above mode (4) may be embodied in a form that the first and the second scanner scan the respective light beams using a common optical element (e.g., a common mirror).

(5) The apparatus according to the mode (4), wherein the angle modifying device and the second scanner have an optical conjugate relationship therebetween.

(6) The apparatus according to any one of the modes (1) to (5), wherein the guiding device includes:

a mirror arranged in front of the pupil; and a relay optical system for introducing the light beam scanned by the scanning device into the mirror, such that an exit position at which the light beam exits from the scanning device and a position of the pupil have an optical conjugate relationship therebetween.

(7) The apparatus according to any one of the modes (1) to (6), wherein the angle modifying device includes, a mirror arranged at a position having an optical conjugate relationship with a position of the pupil, and the apparatus further comprising a relay optical system for introducing the light beam scanned by the scanning device into the mirror, and wherein an exit position at which the light beam exits from the scanning device and a position of the mirror have an optical conjugate relationship therebetween.

(8) The apparatus according to any one of the modes (1) to (7), wherein the angle modifying device modifies the pupil incident angle using an optical element common to the angle modifying device and the scanning device.

The apparatus according to the above mode (8) makes it possible to reduce the apparatus in total number of components thereof and in size more easily than when the angle modifying device and the scanning device are constructed independently of each other by employing separate optical elements.

The "angle modifying device" set forth in the above mode (8) may share an optical element with at least one of the first and the second scanner, in the event that the scanning device includes the first and the second scanner and the relay optical system, like in the above-described mode (4).

In addition, the "angle modifying device" set forth in the above mode (8) may share an optical element with the scanning device, in the event that the scanning device is constructed such that the first and the second scanner share an optical element with each other.

(9) The apparatus according to any one of the modes (1) to (8), wherein the scanning device includes:

a first scanner for scanning the light beam in a first scanning direction; and a second scanner for scanning the light beam in a second scanning direction intersecting the first scanning direction at a lower speed than the first scanner scans, and wherein the angle modifying device modifies the pupil incident angle using an optical element common to the angle modifying device and the second scanner.

The apparatus according to the above mode (9) requires fewer modifications to which the scanning device is subject in an attempt to share an optical element with the angel modifying device than when the angle modifying device is attempted to share an optical element with the first scanner scanning the light beam at a higher speed than the second scanner.

(10) The apparatus according to any one of the modes (1) to (9), wherein a set of the scanning device, the guiding device, and the angle modifying device is provided for each of a pupil of a right eye and a pupil of a left eye of the viewer, and the apparatus further comprising:

a setting device for setting a display position at which the image is displayed in the form of a virtual image in front of the pupils of the eyes, in response to an externally input command; and a controller for controlling the two angle modifying devices for the pupils of the right and left eyes, respectively, such that two extended center lines intersect each other at the set display position, wherein each of the two extended center lines is defined by extending back the center line of the light beam entering each of the two pupils from a corresponding one of the two guiding devices.

In the apparatus according to the above mode (10), the controller effects a control for both angle modifying devices respectively provided for the viewer's right and left pupils. As a result of the control, both angle modifying devices modify the angles of the center lines of the scanning angles of the respective scanning devices, such that two extended lines intersect each other at a desired display position designated using the setting device, wherein each of the two extended lines is obtained by extending back the center line of the scanning angle entering the corresponding pupil from the corresponding guiding device.

Therefore, the apparatus according to the above mode (10) allows a modification of the angle of the center line of the scanning angle of the light beam entering each guiding device, such that a virtual image is displayed at a desired display position designated via the setting device, namely, such that the viewer perceives that a virtual image is displayed at the desired display position, with the desired display position coincident with the convergence point of the viewer's both eyes.

The "display position at which the image is displayed in the form of a virtual image in front of the pupils of the eyes" set forth in the above mode (10) means a position a predetermined length apart from the pupils.

(11) The apparatus according to the mode (10), wherein the setting device includes:

a sight-line sensor for detecting sight lines of the right and left eyes of the viewer; and means for setting the display position to a position at which the sight lines detected by the sight-line sensor intersect each other.

The apparatus according to the above mode (11) allows a desired display position of a virtual image to be set so as to coincide with the intersection of the viewer's right and left sight lines detected by the sight-line sensor, namely, the actual position of the convergence point of the viewer's both eyes.

Further, the apparatus allows a change in the angle of the center line of the scanning angle of the light beam entering each guiding device such that a virtual image is displayed at the thus set desired display position.

(12) The apparatus according to the mode (10), wherein the setting device is constituted to set a desired display position of the image to any position in response to manipulation of the viewer.

The apparatus according to the above mode (12) allows the viewer to set a desired display position of a virtual image at any position in front of the pupils.

Further, the apparatus allows a change in the angle of the center line of the scanning angle of the light beam entering each guiding device such that a virtual image is displayed at the thus set desired display position.

In the apparatus according to the above mode (12), the setting of a desired display position depending on the viewer's manipulation may be performed using such as a switch or the equivalents thereof (e.g., a button, a slide switch, a dial, etc.) permitting a designation of a desired display position at different positions; an input key permitting an entry of a desired display position in a numerical value (representing the distance from the pupils); etc.

(13) The apparatus according to the mode (10) or (12), further comprising:

a wave-front-curvature modulator for modulating a wave front curvature of the light beam leaving the light beam generator and entering the scanning device; and a commanding device for providing a command to the wave-front-curvature modulator to attain a value of the wave front curvature in accordance with a distance from a position of the two pupils to the display position set by the setting device.

In the apparatus according to the above mode (13), the wave-front-curvature modulator modifies the curvature of the wave front of the light beam so as to coincide with that corresponding to a distance between the position of the pupils and the desired display position set by the setting device, in response to the command from the commanding device.

In general, the radius of curvature of the wave front of a light beam is represented by the reciprocal of the curvature of the wave front. The smaller the radius of curvature is, the closer to a viewer the viewer perceives a virtual image formed by a light beam. In addition, the desired display position set by the setting device means a position at which a virtual image is displayed.

Therefore, if an modification is made on the radius of curvature of a light beam so as to obtain that corresponding or equal to the distance between the position of a viewer's pupils and the display position of a virtual image, there will become in agreement with each other the actual display position of a virtual image formed by a light beam and a desired display position at which the view desires to view the virtual image. This results in a capability of avoiding the viewer from feeling discomfort due to disagreement between the actual and the desired display position.

In particular, in the event where the setting device contained in the apparatus according to the above mode (13) is capable of setting a desired display position of a virtual image at any position in response to a viewer's manipulation, the apparatus allows the viewer to cause the virtual image to be displayed at a position at which the viewer can bring the viewer's eyes into focus and which depends on the viewer's vision.

(14) The apparatus according to the mode (11), further comprising:

a wave-front-curvature modulator for modulating a wave-front-curvature of the light beam leaving the light beam generator and entering the scanning device; and means for controlling the wave-front-curvature modulator to attain a value of the wave front curvature in accordance with a distance from a position of the two pupils to a position at which the sight lines detected by the sight-line sensor intersect each other.

In the apparatus according to the above mode (14), the wave-front-curvature modulator as controlled by the controller modifies the curvature of the wave front of the light beam so as to coincide with that corresponding to the distance between the position of the viewer's pupils (the position corresponding to the pupils) and the intersection of the viewer's right and left sight lines detected by the sight-line sensor.

As described above, the radius of curvature of the wave front of a light beam is represented by the reciprocal of the curvature of the wave front, and the smaller the radius of curvature is, the closer to a viewer the viewer perceives a virtual image based on a light beam. In addition, the intersection of the viewer's right and left sight lines detected by the sight-line sensor means the actual position of the convergence point of the viewer's both eyes.

Therefore, if an modification is made on the radius of curvature of a light beam so as to obtain that corresponding or equal to the distance between the position of a viewer's pupils and the intersection of the viewer's right and left sight lines detected by the sight-line sensor, there will become in agreement with each other the actual display position of a virtual image based on a light beam and the actual position of the convergence point of the viewer's both eyes.

This allows a virtual image to be displayed at a position at which the viewer brings the viewer's eyes in focus, without causing the viewer to feel discomfort due to disagreement between the actual display position and the actual convergence point.

(15) The apparatus according to the mode (13), wherein the wave-front-curvature modulator includes:

a lens for converging the light beam output by the light beam generator;

a mirror for reflecting the light beam converged by the lens to the scanning device again through the lens; and a distance modifier for modifying a distance between the lens and the mirror, to thereby change the wave front curvature of the light beam.

(16) The apparatus according to the mode (14), wherein the wave-front-curvature modifier includes:

a lens for converging the light beam output by the light beam generator;

a mirror for reflecting the light beam converged by the lens to the scanning device again through the lens; and a distance modifier for modifying a distance between the lens and the mirror, to thereby change the wave front curvature of the light beam.

(17) An apparatus for introducing a light beam into a pupil of an eye of a viewer, to thereby project an image onto a retina of the eye, the apparatus comprising:

a light beam generator for generating and outputting a light beam corresponding to the image;

a scanning device for scanning the light beam output by the light beam generator, including:

a first scanner for scanning the light beam in a first scanning direction; and a second scanner for scanning the light beam scanned by the first scanner in a second scanning direction intersecting the first scanning direction;

a guiding device for guiding the light beam scanned by the scanning device toward the pupil; and an angle modifying device for modifying a pupil incident angle at which a center line of a scanning angle of the scanning device enters the pupil, the angle modifying device including a mirror for receiving the light beam scanned by the scanning device, wherein the first and the second scanner have an optical conjugate relationship therebetween, wherein the second scanner and the mirror have an optical conjugate relationship therebetween, and wherein the mirror and a position of the pupil have an optical conjugate relationship therebetween.

The apparatus according to the above mode (17) makes it possible to provide the functions and effects fundamentally in common with the apparatus according to the above mode (1), (2), (4), (5) or (6).

(18) The apparatus according to the mode (17), wherein the angle modifying device modifies the pupil incident angle using an optical element common to the angle modifying device and the scanning device.

The apparatus according to the above mode (18) makes it possible to provide the functions and effects fundamentally in common with the apparatus according to the above mode (8).

(19) An image display program executed by a computer for displaying an image using the apparatus according to any one of the above modes (1) to (18).

The execution of the image display program according to the above mode (19) by a computer makes it possible to provide the functions and effects in common with the apparatus according to any one of the above modes (1) to (18).

(20) An image display program executed by a computer for displaying an image using the apparatus according to the above mode (10), comprising:

a setting step of setting a display position at which the image is displayed in the form of a virtual image in front of the pupils of the eyes, in response to an externally input command; and a controlling step of controlling the two angle modifying devices for the pupils of the right and left eyes, respectively, such that two extended center lines intersect each other at the set display position, wherein each of the two extended center lines is defined by extending back the center line of the light beam entering each of the two pupils from a corresponding one of the two guiding devices.

The execution of the image display program according to the above mode (20) by a computer makes it possible to provide the functions and effects in common with the apparatus according to the above mode (10).

(21) The image display program according to the mode (20), wherein the setting step includes:

a detecting step of detecting sight lines of the right and left eyes of the viewer; and a step of setting the display position to a position at which the sight lines detected in the detecting step intersect each other.

The execution of the image display program according to the above mode (21) by a computer makes it possible to provide the functions and effects in common with the apparatus according to the above mode (11).

(22) The image display program according to the mode (20), wherein the setting step includes a step of setting a desired display position of the image to any position in response to manipulation of the viewer.

The execution of the image display program according to the above mode (22) by a computer makes it possible to provide the functions and effects in common with the apparatus according to the above mode (12).

(23) An image display program executed by a computer for displaying an image using the apparatus which is constructed according to the mode (10) or (12) and which includes a wave-front-curvature modulator for modulating a wave-front-curvature of the light beam leaving the light beam generator and entering the scanning device, the image display program comprising a commanding step of providing a command to the wave-front-curvature modulator to attain a value of the wave front curvature in accordance with a distance from a position of the two pupils to the display position set in the setting step.

The execution of the image display program according to the above mode (23) by a computer makes it possible to provide the functions and effects in common with the apparatus according to the above mode (13).

(24) An image display program executed by a computer for displaying an image using the apparatus which is constructed according to the mode (11) and which includes a wave-front-curvature modulator for modulating a wave-front-curvature of the light beam leaving the light beam generator and entering the scanning device, the image display program comprising a controlling step of controlling the wave-front-curvature modulator to attain a value of the wave front curvature in accordance with a distance from a position of the two pupils to a position at which the sight lines detected in the detecting step intersect each other.

The execution of the image display program according to the above mode (24) by a computer makes it possible to provide the functions and effects in common with the apparatus according to the above mode (14).

It is to be added that the image display programs described so far may be each provided directly with the corresponding image display apparatus according to any one of the above modes, or indirectly with the above apparatus, through an intervening indepentent device, via a recording medium such as an FD, a CD-ROM, a memory card, etc., or a communication network such as the Internet, for example.

The computer suitable for use in executing any one of the above image display programs may be such as a computer incorporated into the corresponding image display apparatus, a computer connected with the corresponding image display apparatus by wire or wireless so as to permit a data-communication therebetween, etc.

Several presently preferred embodiments of the invention will be described in detail by reference to the drawings in which like numerals are used to indicate like elements throughout.

First Embodiment

Referring first to FIG. 1, there is shown an image display apparatus 1 constructed according to a first embodiment of the invention. The image display apparatus 1 is adapted to cause light beams to enter the pupils P (PR: the pupil of the viewer's right eye ER, PL: the pupil of the viewer's left eye EL) of a user of the image display apparatus 1, i. e., a viewer, and to project an image onto the viewer's retinas, for thereby permitting the viewer to perceive a virtual image in front of the pupils PR, PL. The image display apparatus 1 is called "retinal scanning display."

The image display apparatus 1 is equipped with a light-beam generating subsystem 10 for producing and outputting a light beam corresponding to an image to be displayed, i.e., for generating the light beam; and a collimating optical subsystem 30 for transforming the light beam which was output from the light-beam generating subsystem 10 and which passed through an optical fiber 20, into a parallel light.

The image display apparatus 1 is further furnished with a curvature modulating subsystem 40 capable of modulating a wave front curvature of the light beam which has been formed as a parallel light by the collimating optical subsystem 30; and a scanning subsystem 50 for scanning the light beam emitted from the curvature modulating subsystem 40 so that the light beam is projected to form an image.

The image display apparatus 1 is still further equipped with an angle modifying subsystem 60 capable of modifying a pupil incident angle at which the center line of the scanning angle of the scanning subsystem 50 enters the pupil P; and a light-beam guiding subsystem 70 for guiding the light beam emitted from the angle modifying subsystem 60, into the pupil P.

A set of the light-beam generating subsystem 10; the optical fiber 20; the collimating optical subsystem 30; the curvature modulating subsystem 40; the scanning subsystem 50; the angle modifying subsystem 60; and the light-beam guiding subsystem 70, as each described above, is provided for the right pupil PR and the left pupil PL, respectively.

The image display apparatus 1 is further provided with a control panel 80 permitting the viewer to perform various manipulations; a control subsystem 90 for controlling the entire operation of the image display apparatus 1; and so on, all in common with the right and left pupils PR, PL.

As shown in FIG. 1, the light-beam generating subsystem 10 includes, for generating three colored light beams; a B laser 11 for generating a blue light beam, and a B laser driver 12 for driving the B laser 11; a G laser 13 for generating a green light beam, and a G laser driver 14 for driving the G laser 13; and an R laser 15 for generating a red light beam, and an R laser driver 16 for driving the R laser 15.

The light-beam generating subsystem 10 further includes a dichroic mirror 17 for combining the light beams emitted from the lasers 11, 13, 15; and a combining optical system 18 for introducing the light beam combined by the dichroic mirror 17 into the optical fiber 20.

The light-beam generating subsystem 10 is adapted to drive the lasers 11, 13, 15 via respective laser drivers 12, 14, 16, based on color signals output from the control subsystem 90 as a result of execution of an image display program (shown in FIG. 5) as described later, for thereby generating the light beam corresponding to an image and output it into the optical fiber 20.

Figure 2:
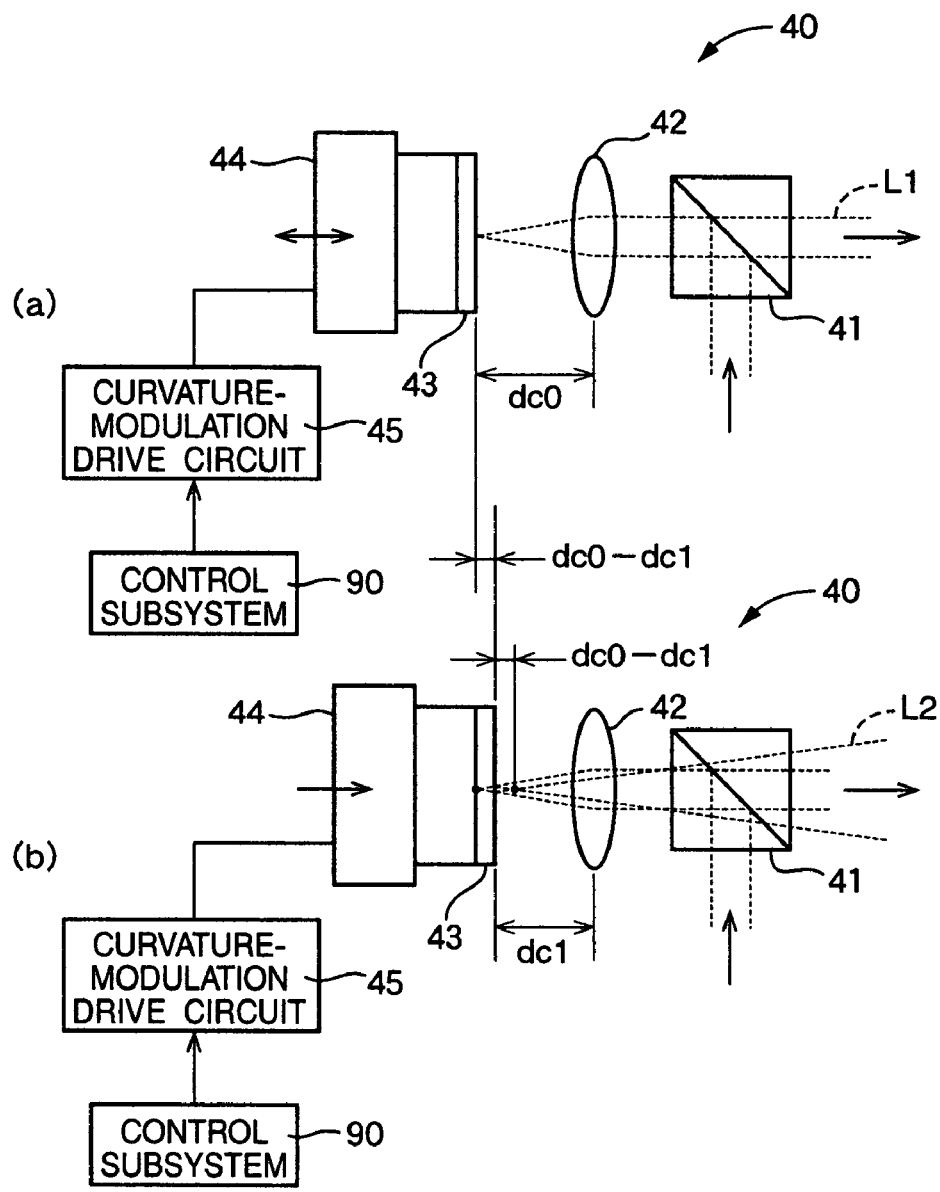
FIG. 2 is a front view for explaining a constitution and an operation of a curvature modulating subsystem indicated in FIG. 1.

As shown in FIG. 2, the curvature modulating subsystem 40 includes a beam splitter 41 for reflecting and transmitting the light beam introduced thereinto from the outside; a convex lens 42 for converging the light beam introduced thereinto via the beam splitter 41; and a mirror 43 for reflecting the light beam converged by the convex lens 42.

The curvature modulating subsystem 40 is further equipped with an actuator 44 for moving the mirror 43 toward or away from the convex lens 42; and a curvature-modulation drive circuit 45 for driving the actuator 44.

In the thus constructed curvature modulating subsystem 40, the light beam introduced thereinto from the collimating optical subsystem 30 is reflected off at the beam splitter 41, passes through the convex lens 42, and is reflected back at the mirror 43. Then, the light beam passes again through the convex lens 42, is transmitted by the beam splitter 41, and travels toward the scanning subsystem 50.

The curvature modulating subsystem 40 is capable of changing a distance dc between the convex lens 42 and the mirror 43 using the actuator 44, for thereby modulating the wave front curvature of the light beam which was introduced thereinto from the collimating optical subsystem 30 and which is traveling toward the scanning subsystem 50.

As shown in FIG. 2(a), when the distance dc between the mirror 43 and the convex lens 42 coincides with a predetermined initial value dc0, the light beam emitted from the collimating optical subsystem 30 is focused and reflected back at a reflective surface of the mirror 43. The reflected light beam travels through the convex lens 42 toward the scanning subsystem 50 in the form of a parallel light L1 having the same wave front curvature as that at the entry into the collimating optical subsystem 30.

Alternatively, as shown in FIG. 2(b), when the distance dc has been changed into a distance dc1 smaller than the initial value dc0, the light beam is reflected back at the reflective surface of the mirror 43 before the light beam is focused, because the mirror 43 is positioned short of the focal point of the convex lens 42. The reflected light beam is focused at a distance (dc0–dc1) apart from the mirror 43 on the near side of the convex lens 42, and subsequently, travels through the convex lens 42 toward the scanning subsystem 50 in the form of a diffused light L2 which is large in the wave front curvature thereof, while which is small in the radius of curvature of the wave front thereof. The diffused light is more diffused than when the diffused light was emitted from the collimating optical subsystem 30.

To sum up the above, the smaller the distance dc becomes, the smaller the radius of curvature of the light beam traveling from the curvature modulating subsystem 40 toward the scanning subsystem 50 becomes. In the present embodiment of the invention, with the initial value dc0 of the distance dc has been set to 4 mm, the image display apparatus 1 is constituted such that, as a reduction in the distance dc from the initial value dc0 is changed from zero into 30 $\mu$m, the curvature radius of the light beam is changed from infinity (in the case of a parallel light) into 0.3 m.

Generally, the radius of curvature of the wave front of a light beam is defined by the reciprocal of the curvature of the wave front, and the smaller the curvature radius is, the closer to a viewer a position at which the viewer perceives a virtual image based on the light beam is. It follows from the above that the smaller the distance dc is made by the actuator 44, the closer to the viewer a position at which the viewer perceives the virtual image becomes.

As shown in FIG. 1, the scanning subsystem 50 is adapted to scan the light beam introduced thereinto from the curvature modulating subsystem 40 so that the light beam is projected to form an image.

For this end, the scanning subsystem 50 is equipped with, for achieving a horizontal scanning: a polygon mirror 51 for scanning in a horizontal direction the light beam introduced thereinto from the curvature modulating subsystem 40; a horizontal scanning motor 52 for driving the polygon mirror 51 in a rotary motion; and a horizontal-scanning drive circuit 53 for driving the horizontal scanning motor 52 in response to a command from the control subsystem 90.

The scanning subsystem 50 is further furnished with, for achieving a vertical scanning: a galvano mirror 54 for scanning in a vertical direction the light beam scanned by the polygon mirror 51 and for outputting the scanned light beam; a vertical scanning actuator 55 for driving the galvano mirror 54; and a vertical-scanning drive circuit 56 for driving the vertical scanning actuator 55 in response to a command from the control subsystem 90.

The scanning subsystem 50 is further provided with a first relay optical system 57 for relaying the light beam between the polygon mirror 51 and the galvano mirror 54. The first relay optical system 57 is an optical system which is arranged to have an optical conjugate relationship between a position within the polygon mirror 51 at which the light beam is introduced thereinto from the curvature modulating subsystem 40, and the center of a reflective surface of the galvano mirror 54. In the scanning subsystem 50, the light beam introduced thereinto from the curvature modulating subsystem 40 is horizontally scanned by the polygon mirror 51, and is vertically scanned by the galvano mirror 54, and subsequently, travels toward the angle modifying subsystem 60.

Figure 3:
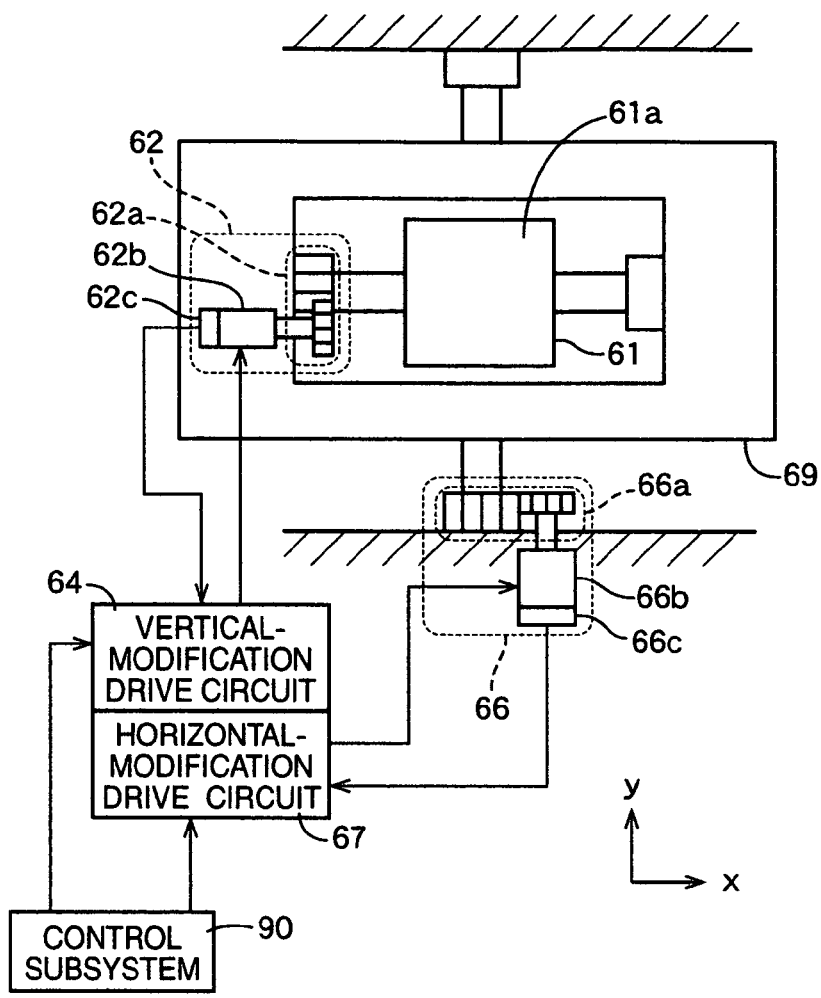
FIG. 3 is a front view illustrating an angle modifying subsystem indicated in FIG. 1.

As shown in FIG. 3, the angle modifying subsystem 60 is equipped with an angle modifying mirror 61 for reflecting the light beam introduced thereinto from the scanning subsystem 50; a vertically modifying mechanism 62 for modifying an angle (reflecting angle) of the direction of the light beam reflected from a reflective surface 61a of the angle modifying mirror 61 in a vertical direction (vertically in FIG. 3), by inclining the reflective surface 61a; and a vertical-modification drive circuit 64 for driving the vertically modifying mechanism 62 in response to a command from the control subsystem 90.

The angle modifying subsystem 60 is further furnished with a horizontally modifying mechanism 66 for modifying an angle (reflecting angle) of the direction of the light beam reflected from the reflective surface 61a of the angle modifying mirror 61 in a horizontal direction (laterally in FIG. 3), by inclining the reflective surface 61a; and a horizontal-modification drive circuit 67 for driving the horizontally modifying mechanism 66 in response to a command from the control subsystem 90.

As shown in FIG. 1, the angle modifying subsystem 60 is further provided with a second relay optical system 68 for relaying the light beam between the galvano mirror 54 of the scanning subsystem 50 and the angle modifying mirror 61. The second relay optical system 68 is an optical system which is arranged to have an optical conjugate relationship between the center of the reflective surface 61a of the angle modifying mirror 61, and the center of the galvano mirror 54 of the scanning subsystem 50.

As shown in FIG. 3, the vertically modifying mechanism 62 includes an inclining device 62a for inclining the reflective surface 61a of the angle modifying mirror 61; a motor 62b for operating the inclining device 62a; and an encoder 62c for detecting an amount of rotation of the motor 62b. On the other hand, the horizontally modifying mechanism 66 includes an inclining device 66a for inclining the reflective surface 61a of the angle modifying mirror 61; a motor 66b for operating the inclining device 66a; and an encoder 66c for detecting an amount of rotation of the motor 66b.

The vertical-modification drive circuit 64 and the horizontal-modification drive circuit 67 are constituted to drive the respective motors 62b, 66b until the amounts of rotations detected by the respective encoders 62c, 66c of the modifying mechanisms 62, 66 become coincident with respective desired amounts of rotations directed by the control subsystem 90.

As shown in FIG. 3, the horizontally modifying mechanism 66 is constituted to incline the reflective surface 61a of the angle modifying mirror 61 by inclining a frame 69 to which the vertically modifying mechanism 62 has been attached together with the angle modifying mirror 61. Therefore, in the angle modifying subsystem 60, the light beam introduced thereinto from the scanning subsystem 50, upon reflection at the angle modifying mirror 61, is directed to the light-beam guiding subsystem 70.

The angle modifying subsystem 60 is capable of modifying an incident angle of the light beam which was reflected from the reflective surface 61a and which attempts to enter the light-beam guiding subsystem 70, by inclining the reflective surface 61a of the angle modifying mirror 61.

In FIG. 4(a), an optical path between the angle modifying mirror 61 and the pupil P is illustrated in an initial state where an angle of inclination of the reflective surface 61a of the angle modifying mirror 61 is coincident with a predetermined initial angle of inclination. A reference direction is defined herein to mean the direction of a scanning center line c0 toward the light-beam guiding subsystem 70. The scanning center line c0 is defined to mean the center line of a scanning angle (deflecting angle) of the light beam reflected at the reflective surface 61a of the angle modifying mirror 61 in the initial state.

As shown in FIG. 4(b), when the angle modifying mirror 61 is rotated from the initial state using the horizontally modifying mechanism 66, about one vertical line passing through the center of the reflective surface 61a, such that the reflective surface 61a of the angle modifying mirror 61 is inclined by an angle $\Delta\alpha$ (or $-\Delta\alpha$), the scanning center line c0 of the light beam reflected from the reflective surface 61a toward the light-beam guiding subsystem 70 is deviated from the reference direction described above by an angle $2\Delta\alpha$ (or $-2\Delta\alpha$) in the same direction as the direction of rotation of the reflective surface 61a.

Alternatively, when the angle modifying mirror 61 is rotated from the initial state using the vertically modifying mechanism 62, such that the reflective surface 61a is inclined by a certain amount of angle, the direction of the scanning center line of the light beam reflected from the reflective surface 61a is deviated from the reference direction in the same direction as the direction of rotation of the reflective surface 61a, as with the above.

Thus, the angle modifying subsystem 60 permits a change in the angle of the scanning center line of the light beam reflected from the reflective surface 61a, i.e., a change in the angle of the center line of the scanning angle of the light beam, by inclining the reflective surface 61a of the angle modifying mirror 61.

As shown in FIG. 1, the light-beam guiding subsystem 70 is equipped with a half mirror 72 located in front of the pupil P; and a third relay optical system 74 for directing the light beam introduced thereinto from the angle modifying subsystem 60, into the half mirror 72. The third relay optical system 74 is an optical system which is arranged to have an optical conjugate relationship between the center of the angle modifying mirror 61 of the angle modifying subsystem 60, and the position of the viewer's pupil P (the position corresponding to the pupil P).

Figure 4:
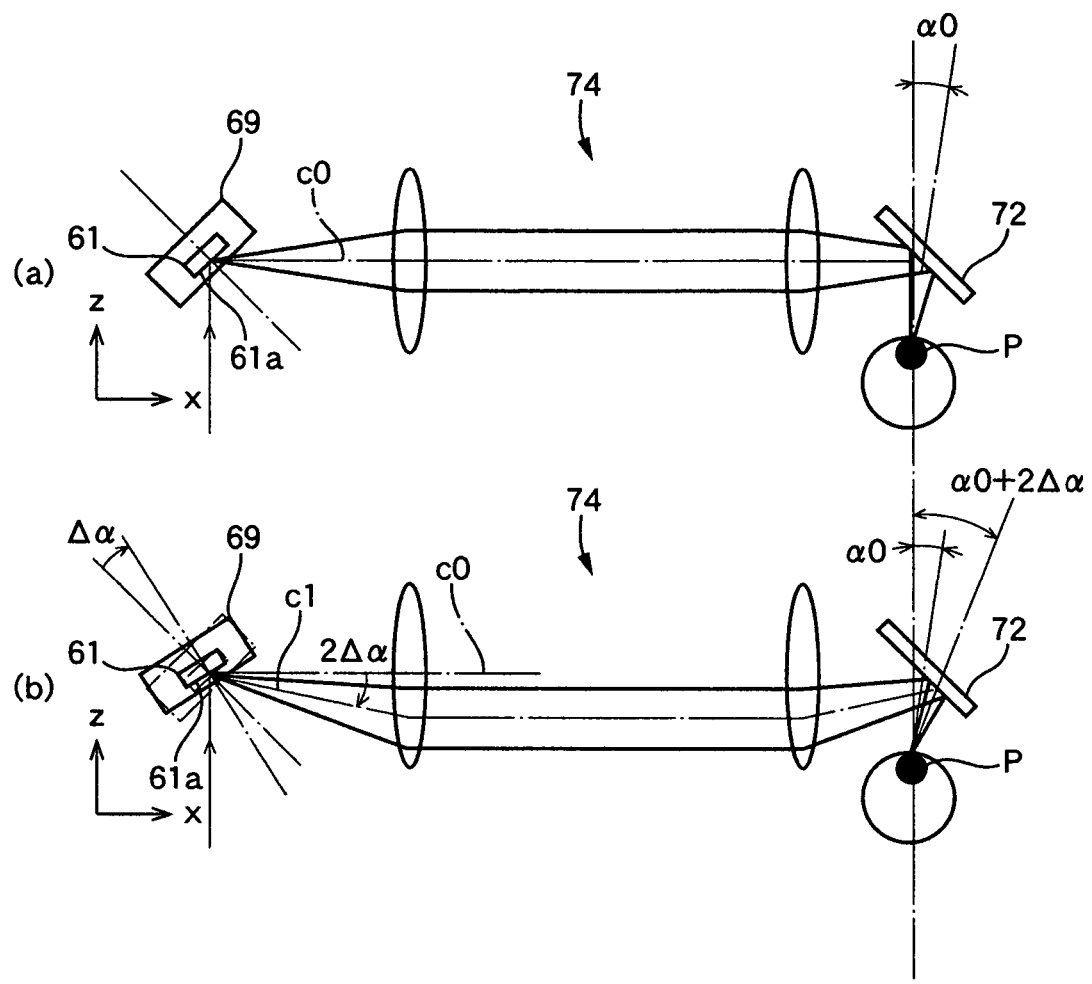
FIG. 4 is an optical ray diagram for explaining a light beam entering a pupil of a viewer through an angle modifying subsystem and a light-beam guiding subsystem in the image display apparatus illustrated in FIG. 1.

In the light-beam guiding subsystem 70, the light beam introduced thereinto from the angle modifying subsystem 60, upon reflection at the half mirror 72, enters the pupil P. The angle of the scanning center line of the light beam thus entering the pupil P is changed, as shown in FIG. 4, from an initial angle $\alpha 0$ into an angle ($\alpha 0 \pm 2\Delta\alpha$) corresponding to the inclination of the angle modifying mirror 61 within the angle modifying subsystem 60.

As shown in FIG. 1, the control panel 80 is equipped with a power switch 82 for activating and deactivating the image display apparatus 1; and a position setting switch 84 for setting a display position of a virtual image as a result of execution of an image display program (shown in FIG. 5) described later.

Figure 5:
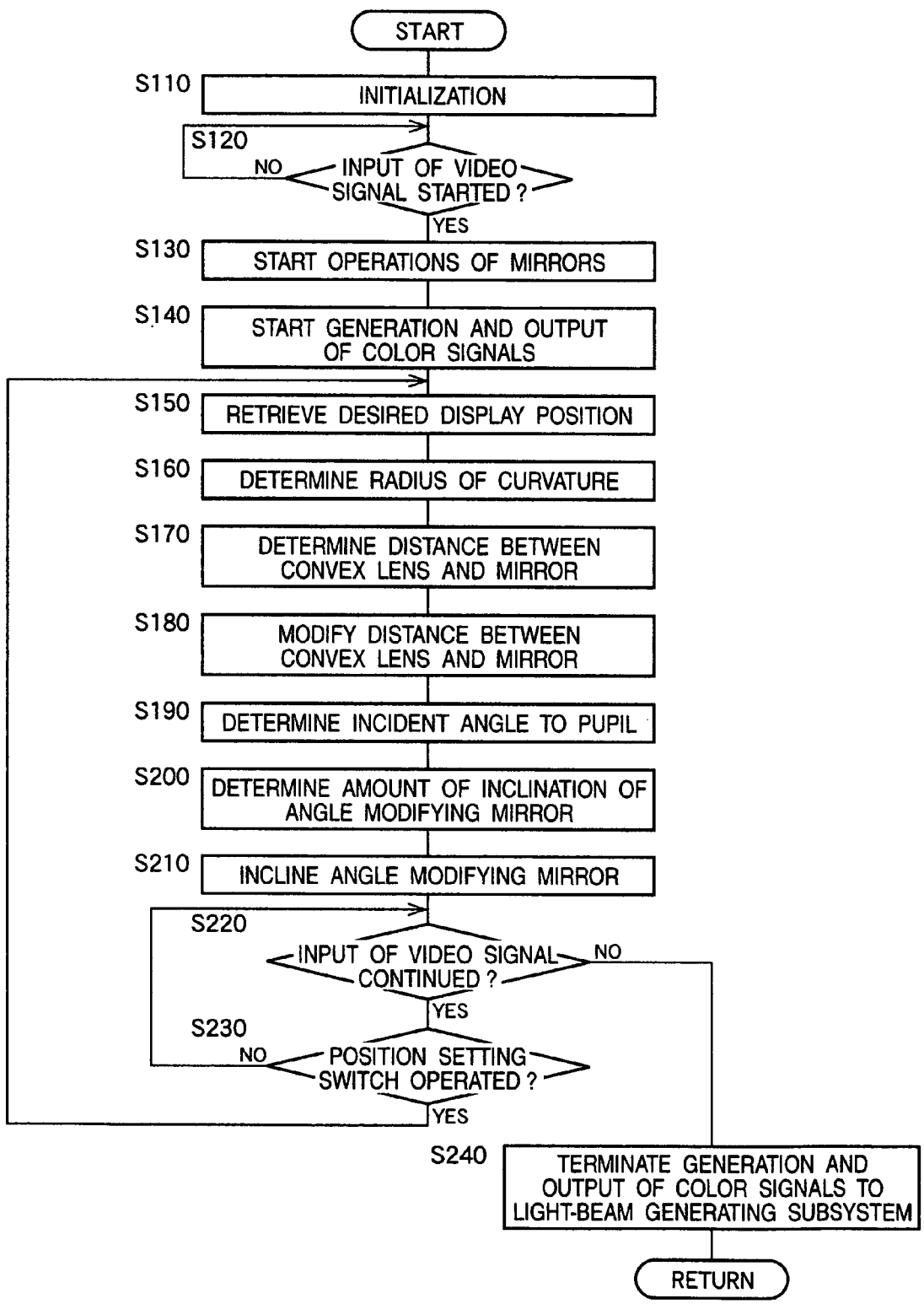
FIG. 5 is a flow chart conceptually illustrating an image display program executed by a computer indicated in FIG. 1.

The position setting switch 84 is a switch for setting a display position at which a virtual image is desired to be displayed (the viewer desires to perceive the display of a virtual image) in front of the pupil P through the execution of the image display program (shown in FIG. 5). The position setting switch 84 permits the settings of desired display positions in a depth direction (z-axis direction), a horizontal direction (x-axis direction), and a vertical direction (y-axis direction).

Figure 6:
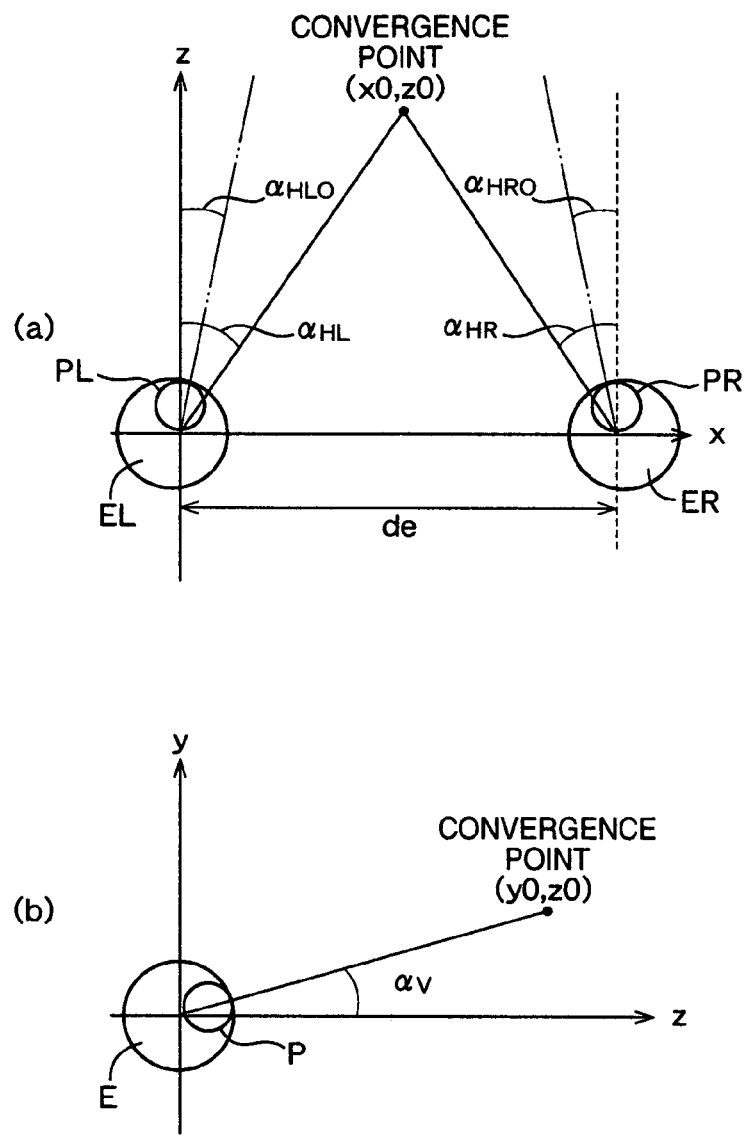
FIG. 6 is a plan view illustrating the viewer's both eyes and a convergence point thereof in a Cartesian coordinate system.

As shown in a plan view of FIG. 6, in the present embodiment of the invention, provided that the center of rotation of the eyeball of the left eye EL corresponds to the origin of coordinate, a desired display position of a virtual image can be set to any position within a range from 0.5 m to infinity (e.g., 10 m) in increments of 0.1 m, in the depth (z-axis) direction. With a depth dimension (a distance measured from the above origin along the depth direction) of a desired display position of a virtual image denoted by z0, a desired display position of a virtual image can be set to any position between ±(z0/2) in increments of (z0/100) m in the horizontal direction, and can also be set to any position between ±(z0/2) in increments of (z0/100) m in the vertical direction.

As shown in FIG. 1, the control subsystem 90 is constructed to mainly incorporate a computer 92 thereinto. The computer 92 is configured to have a processor 94 and a memory 96. The memory 96 has stored the aforementioned image display program therein. The image display program is executed by the processor 94, such that the control subsystem 90 performs an image display process through a predetermined set of procedures, the content of which is conceptually illustrated in a flow chart in FIG. 5.

Upon activation of the image display apparatus 1 by the power switch 82 of the control panel 80, the image display program is repeatedly executed until the image display apparatus 1 is deactivated.

Each cycle of execution of the image display program is started with a step S110 to perform an initialization process.

The initialization process is performed so as to operate the actuator 44 by the curvature-modulation drive circuit 45 within the curvature modulating subsystem 40, for thereby causing the distance dc between the convex lens 42 and the mirror 43 to be coincident with the initial value dc0 (see FIG. 2(a)).

The step S110 is additionally implemented to operate each modifying mechanism 62, 66 by each drive circuit 64, 67 within the angle modifying subsystem 60, for thereby initializing (changing) the angle of inclination of the angle modifying mirror 61 in the angle modifying subsystem 60, such that the angle (angle of the light incident on the pupil P) of the scanning center line of the light beam entering the pupil P from the light-beam guiding subsystem 70 becomes coincident with a predetermined initial angle (see FIG. 4).

As shown in FIG. 6, provided that the rotation center of the eyeball of the viewer's left eye EL corresponds to the origin of coordinate, the angle (angle of the incident light on the pupil P) of the scanning center line formed on the x-z plane, namely, the horizontal plane means, in the case of the left eye EL, an angle $\alpha_{HL}$ formed between a line connecting the aforementioned origin of coordinate and the above convergence point (x0, z0), and the z-axis; while in the case of the right eye ER, an angle $\alpha_{HR}$ formed between a line extending from the center of the rotation of the eyeball in parallel with the z-axis and a line connecting the above center of rotation and the above convergence point.

In addition, the angle (angle of the incident light on the pupil P) of the scanning center line formed on the y-z plane, namely, the vertical plane means an angle $\alpha_V$ formed between a line connecting the above origin of coordinate and the above convergence point (y0, z0), and the z-axis.

Therefore, the step S110 in FIG. 5 is implemented to modify the angle of inclination of the angle modifying mirror 61 of the angle modifying subsystem 60 such that the above-mentioned angles (angles of the incident light on the pupil P) of the scanning center lines $\alpha_{HL}$, $\alpha_{HR}$, and $\alpha_V$ become respectively coincident with predetermined initial angles $\alpha_{HL0}$, $\alpha_{HR0}$, and 0.

The step S110 is further implemented to initialize variables P1, P2, P3 and P4. Specifically, P1 is set to 1(1→P1), P2 is set to $\alpha_{HL0}$ ($\alpha_{HL0}$→P2), P3 is set to $\alpha_{HR0}$ ($\alpha_{HR0}$→P3), and P4 is set to 0(0→P4). Values to which the variables P1, P2, P3 and P4 have been set will be denoted by p1, p2, p3 and p4, respectively.

The step S110 is followed by a step S120 in which the computer 92 waits until a video signal has been started to be externally input. When there is no input to be started, a determination of the step S120 becomes negative "NO," and this step S120 is implemented again.

Once the input of the video signal has been started, the determination of the step S120 becomes affirmative "YES", the following step S130 is implemented to initiate operations of the polygon mirror 51 and the galvano mirror 54. The step S130 is implemented to operate the horizontal scanning motor 52 by the horizontal-scanning drive circuit 53, for thereby initiating an operation of the polygon mirror 51 and to operate the vertical scanning actuator 55 by operation of the vertical-scanning drive circuit 56, for thereby initiating an operation of the galvano mirror 54.

Subsequently, a step S140 is implemented to start a generation of color signals (for blue, green and red light beams) on the basis of an image represented by the video signal input in the step S130, and to start outputting the color signals to the light-beam generating subsystem 10.

In the light-beam generating subsystem 10, upon reception of the color signals, the laser drivers 12, 14, and 16 drive the respective lasers 11, 13 and 15 on the basis of the color signals, resulting in emission of the light beams from the lasers 11, 13, and 15. The emitted light beams, after combined together by the dichroic mirror 17, are output to the optical fiber 20 through the combining optical system 18.

Thereafter, a step S150 is implemented to retrieve a desired display position designated using the position setting switch 84 of the control panel 80. Specifically, the step S150 is implemented to retrieve values indicative of display positions designated using the position setting switch 84 with regard to the depth direction, the horizontal direction and the vertical direction, respectively.

The step S150 is followed by a step S160 to determine the radius of curvature of the light beam entering the pupil P, based on the desired display position retrieved during the implementation of the step S150. In the step S160, a value representing the desired display position retrieved in the step S150, in particular with respect to the depth direction, is determined as the radius of curvature.

Subsequently, a step S170 is implemented to determine the distance dc between the convex lens 42 and the mirror 43 of the curvature modulating subsystem 40, such that the radius of curvature of the light beam entering the pupil P becomes coincident with the radius of curvature determined in the previous step S160.

Specifically, on the basis of data for identifying the relationship between the distance dc between the convex lens 42 and the mirror 43, and the radius of curvature of the light beam introduced thereinto from the curvature modulating subsystem 40, which data has been stored in the memory 96 of the control subsystem 90 in the form of a data table or an arithmetic expression. Then, the aforementioned variable P1 is set to a value indicating the distance dc1 (dc1→P1).

Subsequently, a step S180 is implemented to change the distance dc between the convex lens 42 and the mirror 43 so as to coincide with the distance dc1 determined in the step S170.

Particularly, the step S180 is implemented to operate the actuator 44 by means of the curvature-modulation drive circuit 45 of the curvature modulating subsystem 40, to thereby change the distance dc between the convex lens 42 and the mirror 43 so as to coincide with the distance dc1 determined in the step S170. As a result of the implementation of the step S180, the light beam output from the curvature modulating subsystem 40 comes to have the radius of curvature determined in the step S160.

Therefore, when the thus output light beam has entered the pupil P through the scanning subsystem 50, the angle modifying subsystem 60, and the light-beam guiding subsystem 70, the viewer comes to be able to perceive a virtual image based on the light beam in the form of a virtual image positioned ahead by a distance equivalent to the radius of curvature determined in the step S160.

Following that, a step S190 is implemented to determine the angle of the scanning center line of the light beam entering the pupil P, that is to say, an incident angle of the light beam to the pupil P, based on the desired display position obtained in the step S150.

Specifically, the step S190 is implemented to determine the angle of the scanning center line as defined in the x-z plane, namely, the horizontal plane, as shown in FIG. 6(a), by calculation, provided that the center of rotation of the eyeball of the left eye EL corresponds to the origin of coordinate, and provided that a coordinate point (x0, y0, z0) represented by a value z0 related to the depth direction, a value x0 related to the horizontal direction, and a value y0 related to the vertical direction, all of which values are associated with the desired display position obtained in the step S150, corresponds to the convergence point.

The angle $\alpha_{HL}$, which is defined in the horizontal plane as an angle of the scanning center line of the light beam to be caused to enter the pupil PL of the left eye EL, means an angle formed between a line connecting the origin of coordinate and the convergence point, and the z-axis. Therefore, provided that, when the convergence point is located on a vertical plane passing through the z-axis, that is to say, when the convergence point is identified by a coordinate value(0, y0, z), the angle $\alpha_{HL}$ is equal to zero ($\alpha_{HL}$=0), the angle $\alpha_{HL}$ is calculated from the following equation:

$\alpha_{HL}=\tan^{-1}(x0/z0)$

On the other hand, an angle $\alpha_{HR}$, which is defined in the horizontal plane as an angle of the scanning center line of the light beam to be caused to enter the pupil PR of the right eye ER, means an angle formed between a line extending parallel to the z-axis from the center of rotation of the eyeball of the right eye ER, and a line connecting the pupil PR of the right eye ER and the convergence point. Provided that a distance between both pupils PR, PL (i.e., centers of rotations of the eyeballs of the right and left eyes ER, EL) is denoted by "de", and provided that, when the convergence point is located on a vertical plane apart from the z-axis in parallel in the x direction by the same direction as the distance de, namely, when the convergence point is represented by a coordinate value (de, y0, z), the angle $\alpha_{HR}$ is equal to zero ($\alpha_{HR}$=0), the angle $\alpha_{HR}$ is calculated from the following equation:

$\alpha_{HR}=\tan^{-1}((x0-de)/z0)$

Additionally, as shown in FIG. 6(b), the angle of the scanning center line, as measured in the y-z plane, namely, the vertical plane, is determined by calculation.

An angle $\alpha_V$, which is defined in the vertical plane as an angle of the scanning center line of the light beam to be caused to enter the pupil P, means an angle between a line connecting the origin of coordinate and the convergence point, and the z-axis. Therefore, provided that, when the convergence point is located on a horizontal plane passing through the z-axis, namely, when the convergence point is represented by a coordinate value (x0, 0, z), the angle $\alpha_V$ is equal to zero($\alpha_V$=0), the angle $\alpha_V$ is calculated from the following equation:

$\alpha_V=\tan^{-1}(y0/z0)$

Subsequently, a step S200 indicated in FIG. 5 is implemented to determine the desired amount of inclination of the angle modifying mirror 61 within the angle modifying subsystem 60 such that the angle of the scanning center line of the light beam from the light-beam guiding subsystem 70 into the pupil P becomes coincident with the angle determined in the step S190.

Specifically, the step S200 is first implemented for one of the two angle modifying subsystems 60, 60 provided for the pupil PL of the left eye EL, so as to determine the desired amount of inclination of the angle modifying mirror 61 such that the angle of the scanning center line of the light beam from the light-beam guiding subsystem 70 into the pupil PL becomes coincident with the angle determined in the step S190.

Described in more detail, the step S200 is implemented to determine the desired rotation angle, i.e., the desired amount of inclination of the angle modifying mirror 61 for the horizontally modifying mechanism 66 so as to be half of the difference when the value p2 of the variable P2 (currently equal to the initial value $\alpha_{HL0}$) is subtracted from the angle $\alpha_{HL}$ determined in the step S190. The given result is represented as:

$(\alpha_{HL}-p2)/2$

The step S200 is implemented to further determine the desired rotation angle, i.e., the desired amount of inclination of the angle modifying mirror 61 for the vertically modifying mechanism 62 so as to be half of the difference when the value p4 of the variable P4 (currently equal to the initial value: 0) is subtracted from the angle $\alpha_V$ determined in the step S190. The given result is represented as:

$(\alpha_V-p4)/2$

The step S200 is implemented to still further effect a calculation for the other of the two angle modifying subsystems 60, 60 provided for the pupil PR of the right eye ER in a manner similar to the above. That is, the step S200 is implemented to determine the desired rotation angle, i.e., the desired amount of inclination of the angle modifying mirror 61 of the horizontally modifying mechanism 66 so as to be half of the difference when the value p3 of the variable P3 (currently equal to the initial value $\alpha_{HR0}$) from the angle $\alpha_{HR}$ determined in the step S190. The given result is represented as:

$(\alpha_{HR}-p3)/2$

Furthermore, in the step S200, after the desired amount of inclination of the angle modifying mirror 61 has been thus determined, the variable P2 is reset to the angle $\alpha_{HL}$ determined in the step S190 ($\alpha_{HL} \rightarrow$P2), the variable P3 is reset to the angle $\alpha_{HR}$ determined in the same step S190

($\alpha_{HR} \rightarrow$P3), and the variable P4 is reset to the angle $\alpha_V$ determined in the same step S190 ($\alpha_V \rightarrow$P4).

The following step S210 is implemented so as to incline the angle modifying mirror 61 of the angle modifying subsystem 60 by the desired amount of inclination determined in the step S200. In the step S210, the actual amount of inclination of the angle modifying mirror 61 is inclined by the desired amount of inclination determined in the step S200 by operation of the modifying mechanisms 62, 66 via the respective modification drive circuits 64, 67 in the angle modifying subsystem 60.

After the implementation of the step S210, once the light beam from the angle modifying subsystem 60 has entered the pupil P through the light-beam guiding subsystem 70, the viewer can perceive a virtual image formed with the light beam in a direction forming the desired angle of the scanning center line (incident angle to pupil P) as determined in the step S190, namely, at the desired display position designated via the position setting switch 84 in the control panel 80.

The step S210 is followed by a step S220 to determine whether the input of the video signal which was initiated at the step S120 is still continued or not.

If the input of the video signal is still continued, the determination of the step S220 becomes affirmative "YES", and the following step S230 is implemented to determine whether the position setting switch 84 of the control panel 80 has been operated by the viewer or not.

If the position setting switch 84 has been operated, the determination of the step S230 becomes affirmative "YES", and the computer 92 returns to the step S150.

To the contrary, if the position setting switch 84 has not been operated, the determination of the step S230 becomes negative "NO", and the computer 92 returns to the step S220.

After the repeated executions of the steps S150 through S230 in a manner stated above, once the input of the video signal has been terminated, the determination of the step S220 becomes negative "NO", and the following step S240 is implemented to terminate the generation and the output of the color signals which were initiated at the step S140.

Then, one cycle of the execution of the image display program is terminated.

As evidenced from the above, the image display apparatus 1 constructed according to the present embodiment allows the angle modifying subsystem 70 to modify the incident angle at which the scanning center line of the light beam scanned by the scanning subsystem 50 enters the light-beam guiding subsystem 70 (in the step S210 in FIG. 5).

In the angle modifying subsystem 60, owing to the existing optical conjugate relationship between the angle modifying mirror 61 and the position of the pupil P, the light beam from the scanning subsystem 50 into the pupil P via the light-beam guiding subsystem 70 is focused or converged at a fixed position (hereinafter referred to as "focus position"), regardless of any change in the above-defined incident angle.

It follows that the present embodiment eliminates any possibility of the focus position to deviate off the position corresponding to the position of the pupil P, even though the display direction of the virtual image displayed has been greatly modified. The present embodiment accordingly eliminates an inaccuracy in perceiving a virtual image and an incapability of perceiving a virtual image itself, in the event of any change in the display direction of the virtual image displayed. The present embodiment therefore allows the viewer to modify the display direction of the displayed virtual image more freely over a greater range.

Furthermore, the present embodiment allows the modification of the display direction of the displayed virtual image without causing an inaccuracy in perceiving a virtual image or an incapability of perceiving a virtual image itself by modifying the angle of the scanning center line of the light beam by means of the angle modifying subsystem 60. Therefore, the embodiment allows the viewer to modify the display direction of the displayed virtual image more freely over a greater range, by means of a relatively simple approach to optimize the arrangement of the angle modifying mirror 61.

In addition, in the present embodiment, the angle modifying mirror 61 of the angle modifying subsystem 60 is inclined as a result of the execution of the step S210 in FIG. 5. In this stage, a modification is made in the angle of the scanning center line of the light beams from the light-beam guiding subsystems 70, 70 into the respective pupils PR, PL, such that two lines which are given by extending back the respective two scanning center lines of the light beams from the light-beam guiding subsystems 70, 70 respectively corresponding to the right and left eyes ER, EL into the respective pupils PR, PL intersects each other at the desired display position set via the position setting switch 84 of the control panel 80.

Therefore, in the present embodiment, a change is made in the angle of the scanning center line of the light beam entering each light-beam guiding subsystem 70, 70, such that a virtual image is formed at the desired display position, wherein the desired display position set via the position setting switch 84 of the control panel 80 is coincident with the convergence point of the viewer's eyes ER, EL.

Additionally, in the present embodiment, as a result of the execution of the image display program shown in FIG. 5, the desired display position set via the position setting switch 84 of the control panel 80 is retrieved, and the radius of curvature and the angle of the scanning center line are determined based on the retrieved desired display position.

Therefore, the present embodiment allows the viewer to set the desired display position to any position by operating the position setting switch 84 of the control panel 80. For displaying a virtual image at the thus set display position, the angle of the scanning center line of the light beam entering each light-beam guiding subsystem 70, 70 is modified.

Furthermore, in the present embodiment, as a result of the execution of the step S180 shown in FIG. 5, a modification is made, by the curvature modulating subsystem 40 in response to a command from the control subsystem 90, on the actual radius of curvature (curvature of the wave front) of the light beam from the light-beam generating subsystem 10, such that the actual radius becomes coincident with the radius of curvature corresponding to a distance from the position of the pupil P (the position corresponding to the pupil P) to the display position set via the position setting switch 84 of the control panel 80.

Here, the smaller the radius of curvature of a light beam is, the more closely a viewer perceives a virtual image formed by the light beam. On the other hand, the display position set via the position setting switch 84 is where the viewer desires a virtual image to be displayed.

Therefore, the embodiment achieves a coincidence between the position of a virtual image based on the light beam, namely, the actual display position, and a position where the virtual image is desired to be displayed, namely, the desired display position, resulting in elimination of the viewer's incongruous feeling due to a disagreement between the actual and desired display positions.

Described specifically, the present embodiment allows the viewer to set the desired display position of a virtual image to any position according to the viewer's operation of the position setting switch 84, for thereby facilitating the viewer to set the desired display position such that the virtual image is displayed at a position matching the vision in the viewer's eyes ER, EL.

As will be apparently understood from the above, in the present embodiment, the light-beam generating subsystem 10 constitutes one example of the "light beam generator" set forth in the above mode (1), the scanning subsystem 50 constitutes one example of the "scanning device" set forth in the same mode, the light-beam guiding subsystem 70 constitutes one example of the "guiding device" set forth in the same mode, and the angle modifying subsystem 60 constitutes one example of the "angle modifying device" set forth in the same mode or the above mode (2).

Furthermore, in the present embodiment, the angle modifying mirror 61, the vertically modifying mechanism 62 and the vertical-modification drive circuit 64 together constitute one example of the "first modifier" set forth in the above mode (3), and the angle modifying mirror 61, the horizontally modifying mechanism 66 and the horizontal-modification drive circuit 67 together constitute one example of the "second modifier" set forth in the same mode.

Additionally, in the present embodiment, the polygon mirror 51 constitutes one example of the "first scanner" set forth in the above mode (4), the galvano mirror 54 constitutes one example of the "second scanner" set forth in the same mode or the above mode (5), and the first relay optical system 57 constitutes one example of the "relay optical system" set forth in the above mode (4).

In addition, in the present embodiment, the half mirror 72 constitutes one example of the "mirror" set forth in the above mode (6), and the third relay optical system 74 constitutes one example of the "relay optical system" set forth in the same mode.

Furthermore, in the present embodiment, the angle modifying mirror 61 constitutes one example of the "mirror" set forth in the above mode (7), and the second relay optical system 68 constitutes one example of the "relay optical subsystem" set forth in the same mode.

Additionally, in the present embodiment, the position setting switch 84 constitutes one example of the "setting device" set forth in the above mode (10), and a portion of the computer 92 which is assigned to implement the steps S150, S190 and S210 indicated in FIG. 5 constitutes one example of the "controller" set forth in the same mode.

In addition, in the present embodiment, the curvature modulating subsystem 40 constitutes one example of the "wave-front-curvature modulator" set forth in the above mode (13), and a portion of the computer 92 which is assigned to implement the steps S160 through S180 indicated in FIG. 5 constitutes one example of the "commanding device" set forth in the same mode.

Second Embodiment

Figure 7:
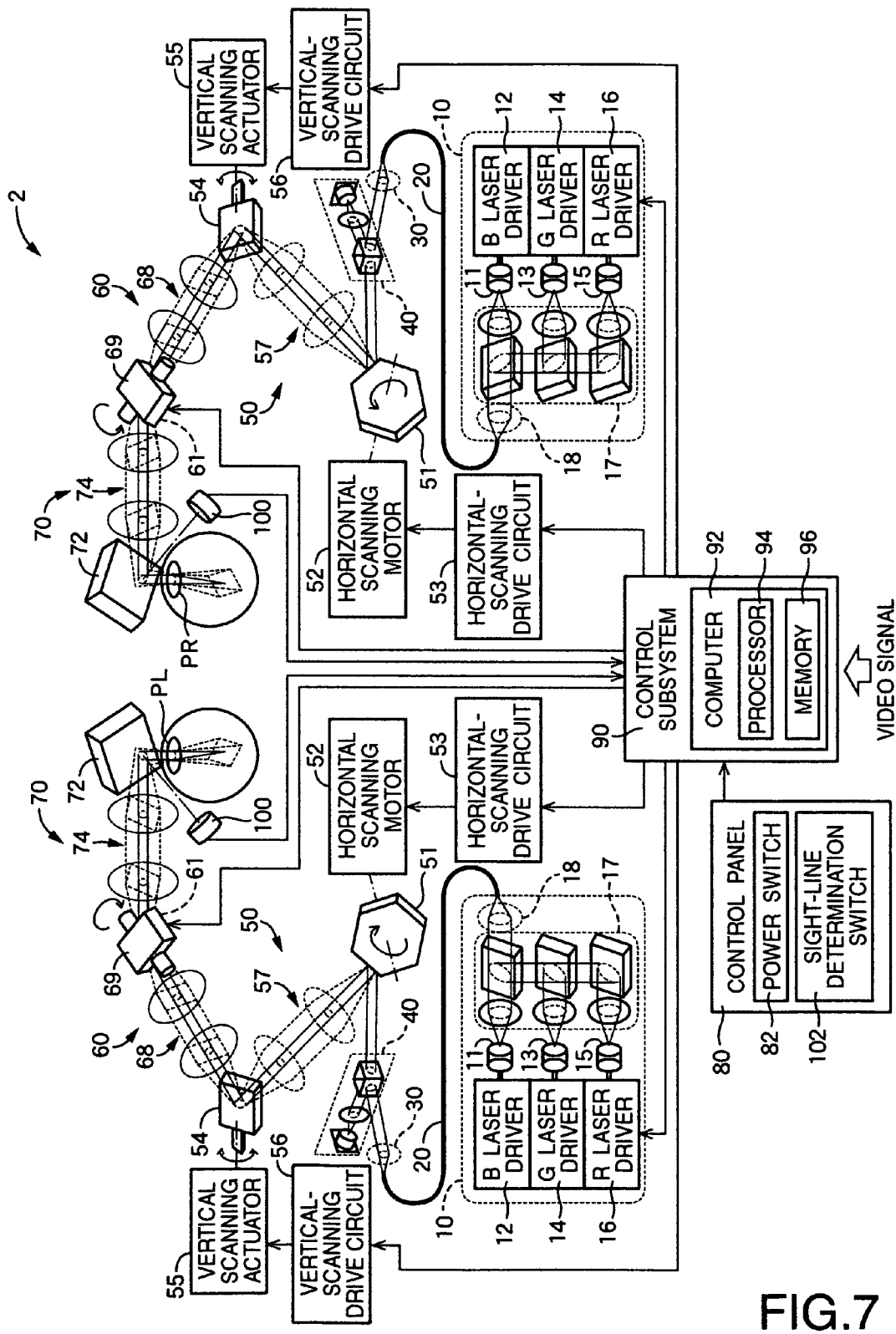
FIG. 7 is a schematic view illustrating an image display apparatus according to a second embodiment of the invention.

Referring next to FIG. 7, there will be described a second embodiment of the present invention. Since the most of the elements used in the second embodiment correspond to those of the first embodiment, the corresponding elements will be identified by referring to the same reference numerals or titles, instead of explaining the corresponding elements in detail, while only the distinctive elements of the second embodiment will be explained in detail.

As shown in FIG. 7, an image display apparatus 2 constructed according to the present invention is equipped with, as with the first embodiment, the light-beam generator 10; the collimating optical subsystem 30; the curvature modulating subsystem 40; the scanning subsystem 50; the angle modifying subsystem 60; the light-beam guiding subsystem 70; the control panel 80; and the control subsystem 90.

The image display apparatus 2 is further furnished with a sight-line sensor 100 which is absent from the first embodiment. The sight-line sensor 100 is so constructed, for detecting the line of sight of the viewer, as to contain a CCD camera for picking up an eye image projected on the half mirror 72 of the light-beam guiding subsystem 70. The CCD camera is adapted to output an image data representing the picked-up eye image to the control subsystem 90.

A set of the light-beam generating subsystem 10; the optical fiber 20; the collimating optical subsystem 30; the curvature modulating subsystem 40; the scanning subsystem 50; the angle modifying subsystem 60; the light-beam guiding subsystem 70; and the sight-line sensor 100, is provided for the right pupil PR and the left pupil PL, respectively.

The control panel 80 is constituted to have the power switch 82 for activating and deactivating the image display apparatus 2, and a sight-line determination switch 102. The sight-line determination switch 102 is a switch provided to be operated for determining a direction of the line of sight for the viewer, wherein the determined direction functions as a reference direction when an image display program described later is executed.

Figure 8:
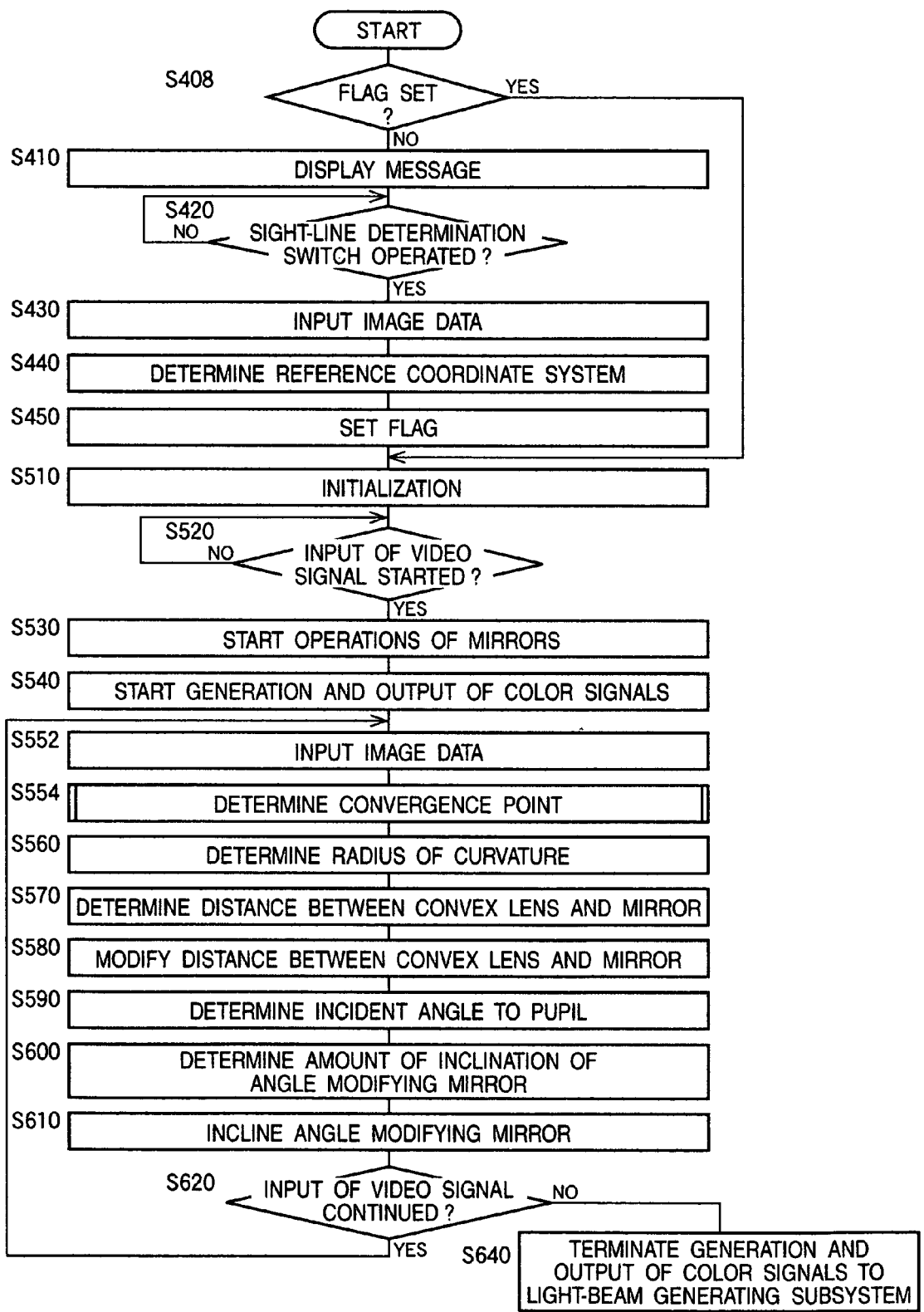
FIG. 8 is a flow chart conceptually illustrating an image display program executed by a computer indicated in FIG. 7.

In FIG. 8, the image display program mentioned above is conceptually illustrated in a flow chart. The image display program, having the steps corresponding to those of the image display program illustrated in FIG. 5, will be explained in detail, only in regard to the distinctive steps thereof, while the image display program will be explained briefly in regard to the corresponding steps thereof.

The image display program in the present embodiment is repeatedly executed by the computer 92 of the control subsystem 90. Each cycle of execution of the image display program is initialized with a step S408 to determine whether a suitable flag has been reset or not. The flag is defined such that the flag indicates incompletion of establishment of a reference coordinate system described later when the flag is in a reset status, while the flag indicates completion of establishment of the reference coordinate system when the flag is in a set status. The flag is initialized to be brought into the reset status in response to the activation of the computer 92. Suppose that the flag is in the reset status, the determination of the step S408 becomes negative "NO", and the computer 92 goes to a step S410.

The step S410 is implemented so as to display to the viewer a message which prompts the viewer to operate the sight-line determination switch 102 of the control panel 80 with the viewer's sight-line directed at a far point.

Particularly, the step S410 is implemented to generate color signals for displaying a message image representing the above message, and is implemented to apply the generated color signals to the light-beam generating subsystems 10, 10 for both eyes ER, EL.

In the light-beam generating subsystem 10, upon reception of the color signals, the laser drivers 12, 14, and 16 drive the respective lasers 11, 13, and 15 on the basis of the respective color signals, resulting in emission of the light beams from the lasers 11, 13, and 15. After combined by the dichroic mirror 17, the emitted light beams are output to the optical fibers 20, 20 through the combining optical systems 18, 18.

The output light beams enter the pupils PR, PL sequentially through the collimating optical subsystems 30, 30; the curvature modulating subsystems 40, 40; the scanning subsystems 50, 50; the angle modifying subsystems 60, 60; and the light-beam guiding subsystems 70, 70, whereby the above message image is perceived by the viewer.

After perceiving the message image in the above manner, the viewer operates the sight-line determination switch 102 of the control panel 80 according to the message indicated in the message image, with the viewer's sight-line directed at a far point.

The step 410 is followed by a step S420 to wait for the viewer to operate the sight-line determination switch 102 of the control panel 80.

Once the sight-line determination switch 102 has been operated, a determination of the step S420 becomes affirmative "YES", and in the following step S430, the aforementioned image data is input from the sight-line sensor 100. At this stage, the images of the right and left eyes ER, EL, which are projected on the half mirrors 72, 72 of the light-beam guiding subsystems 70, 70, are input from the sight-line sensors 100, 100 for both eyes ER, EL.

The step S430 is followed by a step S440 to determine the aforementioned reference coordinate system on the basis of the image data input in the step S430.

Specifically, the step S440 is implemented, for the images of the right and left eyes ER, EL represented by the image data input in the step S430, so as to produce each binary image representing the white and the black of each eye ER, EL in white and black, on the basis of the above image data, respectively for the right and left eyes ER, EL.

Figure 10:
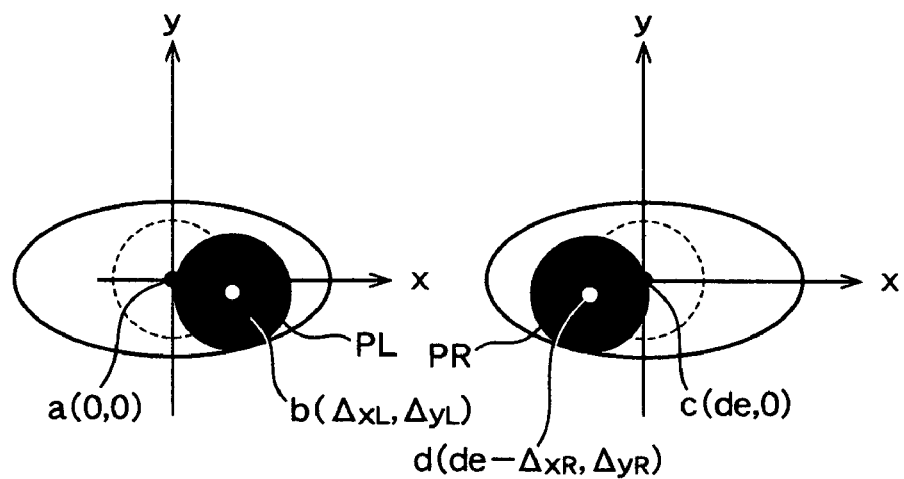
FIG. 10 is a front view illustrating an image of both eyes represented by an image data input from a sight-line sensor indicated in FIG. 7.

The step S440 is further implemented, for the binary image of the left eye EL, as shown in FIG. 10, so as to define the center position of an oval approximating a white area of the binary image which represents the white of the left eye EL in the reference coordinate system, as a first reference position "a" (0, 0) (the origin of the reference coordinate system). The reference coordinate system is formed as a Cartesian coordinate system where a vertical direction of the binary image is taken on the x-axis and a horizontal direction of the binary image is taken on the y-axis.

The step S440 is still further implemented, for the binary image of the right eye ER, as with the above, so as to define the center position of an oval approximating a white area of the binary image which represents the white of the right eye ER in the above reference coordinate system, as a second reference position "c" (de, 0) which is located apart from the origin of the reference coordinate system in the direction of the x-axis by a predetermined distance de between the right and left pupils PR and PL (the rotation centers of the eyeballs of the right and left eyes ER and EL).

Once the reference coordinate system has been thus defined, a step S450 indicated in FIG. 8 is implemented to set the aforementioned flag.

Following that, a step S510 is implemented to effect an initialization. The process is similar to that effected in the step S110 indicated in FIG. 5.

The step S510 is followed by a step S520 to wait until the video signal has been started to be externally input.

Once the input of the video signal has been started, a determination of the step S520 becomes affirmative "YES", and the subsequent step S530 is implemented to start operating the galvano mirror 54 and the polygon mirror 51. The process is similar to that effected in the step S130 indicated in FIG. 5.

Thereafter, a step S540 is implemented to produce the color signals on the basis of the image represented by the video signal, the input of which was started in the step S520. The produced color signals are applied to the light-beam generating subsystems 10, 10. The process is similar to that effected in the step S140 in FIG. 5.

Subsequently, a step S552 is implemented to input the image data again from the sight-line sensor 100. The process is similar to that effected in the step S430.

The step S552 is followed by a step S554 to determine the convergence point of the viewer's sight lines on the basis of the image data input in the step S552. The process is effected for determining the actual convergence point (x0, y0, z0) of the viewer's sight lines.

Figure 9:
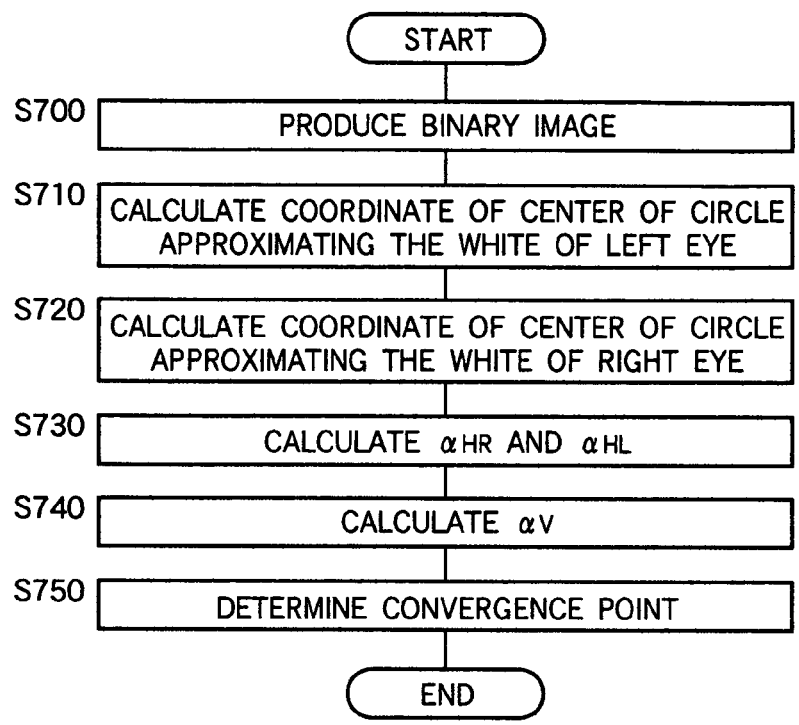
FIG. 9 is a flow chart conceptually illustrating a step S554 indicated in FIG. 8 in the name of a convergence-point determination routine.

Referring next to FIG. 9, the details of the step S554 is conceptually illustrated in the name of "convergence-point determination routine."

The convergence-point determination routine starts with a step S700 to produce the aforementioned binary images on the basis of the images of both eyes ER, EL represented by the image data input in the step S552 for both eyes ER, EL.

The step S700 is followed by a step S710 to calculate the coordinate values of the center position "b" of the circle approximating a black area of the binary image for the left eye EL, wherein the black area represents the black of the left eye EL. Specifically, the step S710 is implemented to calculate, as shown in FIG. 10, the coordinate values of the center position "b" ($\Delta x_L$, $\Delta y_L$) from a predetermined distance between the first reference position "a" determined in the step S440 indicated in FIG. 8, and the above center position "b."

Subsequently, a step S720 indicated in FIG. 9 is implemented to calculate the coordinate values of the center position "d" of the circle approximating a black area of the binary image for the right eye ER, wherein the black area represents the black of the right eye ER. Specifically, the step S720 is implemented to calculate, as shown in FIG. 10, the coordinate values of the center position "d" (de-$\Delta x_R$, $\Delta y_R$) from a predetermined distance between the second reference position "c" determined in the step S440, and the above center position "d."

After the execution of the step S720, a step S730 is implemented to calculate the angle $\alpha_{HL}$, which is formed between a line connecting the aforementioned first reference position "a" and the convergence point of the viewer's sight lines, and the z-axis; and the angle $\alpha_{HR}$, which is formed between a line connecting the aforementioned second reference position "c" and the above convergence point, and the z-axis, both in the x-z plane, namely, a horizontal plane, on the basis of the coordinate values calculated in the steps S710 and S720.

Specifically, the step S730 is implemented to calculate the angles $\alpha_{HL}$ and $\alpha_{HR}$ according to the following equations, given that the radius of the eyeball is denoted by "re":

$$\alpha_{HL}=\sin^{-1}(\Delta x_L/re)$$

$$\alpha_{HR}=\sin^{-1}(\Delta x_R/re)$$

Subsequently, a step S740 is implemented to calculate the angle $\alpha_V$, which is formed between a line connecting the aforementioned first reference point "a" (or the second reference point "c") and the convergence point of the viewer's sight lines, and the z-axis in the y-z plane, namely, a vertical plane, on the basis of the coordinate values calculated in the steps S710 and S720. Described in detail, the step S740 is implemented to calculate the angle $\alpha_V$ according to the following equation:

$$\alpha_V = \sin^{-1}(\Delta y_L / re)$$

Thereafter, a step S750 is implemented to determine the convergence point of the viewer's sight lines on the basis of the angles calculated in the steps S730 and S740.

Specifically, the step S750 is implemented to calculate the x-coordinate value x0 of the convergence point (x0, y0, z0) of the viewer's sight lines, according to the following equation, given that the distance between the right and left pupils PR, PL is denoted by "de":

$$x0 = (de \cdot \tan \alpha_{HL}) / (\tan \alpha_{HL} + \tan \alpha_{HR})$$

Furthermore, the y-coordinate value y0 of the above convergence point (x0, y0, z0) is calculated according to the following equation:

$$y0 = (de \cdot \tan \alpha_V) / (\tan \alpha_{HL} + \tan \alpha_{HR})$$

Still further, the z-coordinate value z0 of the above convergence point (x0, y0, z0) is calculated according to the following equation:

$$z0 = de / (\tan \alpha_{HL} + \tan \alpha_{HR})$$

Then, one cycle of the execution of the sight-line determination routine is terminated.

Thereafter, a step S560 indicated in FIG. 8 is implemented to determine a radius of curvature of the light beam which is caused to enter the pupil P, on the basis of the convergence point determined in the step S554. The process is similar to that effected in the step S160 indicated in FIG. 5.

Subsequently, a step S570 is implemented to determine a desired value of the distance dc between the convex lens 42 and the mirror 43 in the curvature modulating subsystem 40, so as to be a distance dc1 permitting the actual radius of curvature of the light beam entering the pupil P to coincide with the radius of curvature determined in the step S560. The process is similar to that effected in the step S170 indicated in FIG. 5.

The step S570 is followed by a step S580 to change the actual value of the distance dc between the convex lens 42 and the mirror 43 in the curvature modulating subsystem 40 so as to coincide with the desired value of the distance dc1 determined in the step S570. The process is similar to that effected in the step S180 indicated in FIG. 5.

Subsequently, a step S590 is implemented to determine a desired value of the angle of the scanning center line of the light beam which is caused to enter the pupil P. Specifically, in the step S590, a desired value of a horizontal angle (pupil incident angle) $\alpha_{HL}$ of the scanning center line of the light beam which is caused to enter the left pupil PL is determined so as to be the angle $\alpha_{HL}$ calculated in the step S730 indicated in FIG. 9.

Furthermore, a desired value of a horizontal angle (pupil incident angle) $\alpha_{HR}$ of the scanning center line of the light beam which is caused to enter the right pupil PR is determined so as to be the angle $\alpha_{HR}$ calculated in the step S730 indicated in FIG. 9.

Still further, a desired value of a vertical angle $\alpha_V$ of the scanning center line of the light beam entering both eyes PR, PL is determined so as to be the angle $\alpha_V$ calculated in the step S740 indicated in FIG. 9.

Thereafter, a step S600 indicated in FIG. 8 is implemented to determine a desired value of the aforementioned inclination amount of the angle modifying mirror 61 in the angle modifying subsystem 60, such that actual values of the pupil incident angles $\alpha_{HL}$, $\alpha_{HR}$, $\alpha_V$ of the light beam entering the pupil P from the light-beam guiding subsystem 70 is coincident with the desired values of the pupil incident angles $\alpha_{HL}$, $\alpha_{HR}$, $\alpha_V$ determined in the step S590, respectively. The process is similar to that of the step S200 indicated in FIG. 5.

Following that, a step S610 is implemented to incline the angle modifying mirror 61 of the angle modifying subsystem 60 so as to achieve the desired values of the inclination amount determined in the step S600. The process is similar to the step S210 indicated in FIG. 5.

The step S610 is followed by a step S620 to make a determination as to whether the input of the video signal which was started by the execution of the step S520 has been continued or not.

If the input of the video signal has been continued, the determination of the step S620 becomes affirmative "YES", and the computer 92 returns to the step S552.

After several cycles of execution of the steps S552 through S620, if the input of the video signal has been terminated, the determination of the step S620 becomes negative "NO". Following that, a step S640 is implemented to terminate the generation and the output of the color signals which were started by the execution of the step S540. Then, one cycle of the execution of the image display program is terminated.

In the following cycle of the execution of the image display program, the aforementioned flag is in the set status. Therefore, the determination of the step S408 becomes affirmative "YES", and the steps S410 through S440 are skipped. For the reason, a redundant determination of the reference coordinate system described above is avoided.

As evident from the above, the present embodiment, as with the first embodiment, allows the viewer to modify the directional position of the displayed virtual image more freely over a greater range by means of a relatively simple approach to optimize the arrangement of the angle modifying mirror 61.

Furthermore, the present embodiment, as a result of the execution of the step S610 indicated in FIG. 8, allows the angle of the scanning center line of the light beam entering each light-beam guiding subsystem 70, 70 to be modified such that a virtual image is displayed at the display position designated via the position setting switch 84 of the control panel 80.

Therefore, the present embodiment allows the angle of the scanning center line of the light beam entering each light-beam guiding subsystem 70, 70 to be modified such that a virtual image is displayed at the display position set via the position setting switch 84 of the control panel 80, with the convergence point of the viewer's both sight lines located at the designated display position.

Furthermore, in the present embodiment, the image display program indicated in FIG. 5 is executed to retrieve the display position set via the position setting switch 84 of the control panel 80, and to determine the radius of curvature and the angle of the scanning center line on the basis of the retrieved display position.

Still further, the present embodiment allows the viewer to set the desired display position for displaying a virtual image in front of the pupil P to any position by depending on the viewer's operation of the position setting switch 84 of the control panel 80, with the result of that the angle of the scanning center line of the light beam entering each light-beam guiding subsystem 70, 70 is modified such that the virtual image is displayed at the thus set display position.

In addition, in the present embodiment, the convergence point of the viewer's both sight lines is determined on the basis of the image data of both eyes ER, EL represented by the output signal of the sight-line sensor 100. To be more specific, as a result of the execution of the step S750 indicated in FIG. 9, the intersection of the viewer's right and left sightlines, namely, the viewer's actual convergence point is calculated on the basis of the image data of both eyes ER, EL represented by the output signal of the sight-line sensor 100.

Additionally, in the present embodiment, on the basis of the thus determined convergence point, both the radius of curvature of the wave front of the light beam entering each pupil PR, PL, and the angle of the scanning center line, namely, the aforementioned pupil incident angle are determined.

Therefore, the present embodiment allows the viewer to set the desired display position for displaying a virtual image in front of the pupil to any position, provided that the viewer directs the viewer's both sightlines at the desired display position.

Furthermore, in the present embodiment, as a result of the execution of the step S580 indicated in FIG. 8, the curvature modifying subsystem 40 changes the actual radius of curvature (wave front curvature) of the light beam emitted from the light-beam generating subsystem 10, into the radius of curvature corresponding to the distance from the position of the pupil P (position corresponding to the pupil P) in the viewer to the convergence point determined in the step S554.

It is noted that the smaller the value of the radius of curvature of a light beam is, the nearer to a viewer a virtual image based on the light beam is perceived. On the other hand, the convergence point determined in the step S554 means the viewer's actual convergence point.

Therefore, the present embodiment allows an agreement between the position of a virtual image based on the light beam, namely, the actual display position, and the viewer's actual convergence point, resulting in elimination of the viewer's discomfort due to a disagreement between the actual display position and the actual convergence point.

As will be apparently understood from the above, in the present embodiment, the sight-line sensor 100 which is provided for each eye ER, EL, and a portion of the computer 92 which is assigned to execute the step S554 indicated in FIG. 8 together constitute one example of the "setting device" set forth in the above mode (10), and a portion of the computer 92 which is assigned to execute the steps S590 through S610 indicated in FIG. 8 constitutes one example of the "controller" set forth in the same mode.

Additionally, in the present embodiment, the sight-line sensor 100 constitutes one example of the "sight-line sensor" set forth in the above mode (11), and a portion of the computer 92 which is assigned to execute the step S554 indicated in FIG. 8 constitutes one example of the "means for setting the display position" set forth in the same mode.

Having described the invention in the first and the second embodiment thereof, the invention may be embodied in several forms with various changes and modifications in addition to the above first and the second embodiment.

For example, the invention is embodied in the first and the second embodiment such that all of the steps of the aforementioned image display program are implemented by the computer 92 contained in the control subsystem 90. Alternatively, the invention may be embodied in a form that all or a part of the above steps are implemented by a computer which is physically independent from the corresponding image display apparatus 1, 2, and which is connected by wire or wireless to the corresponding image display apparatus 1, 2.

Additionally, the invention is embodied in the first and the second embodiment such that the aforementioned image display program is read out from the memory 96 contained in the control subsystem 90, and in turn, is executed by the computer 92. Alternatively, the invention may be embodied in a form that, where the computer 92 is constituted to read out data from and write data onto a removable recording medium, such as an FD, a memory card, etc., the image display program to be executed by the computer 92 is read out from the recording medium and then is executed, by the computer 92.

Furthermore, the invention is embodied in the first and the second embodiment such that the scanning subsystem 50 is constituted to contain both the polygon mirror 51 for achieving a principal or horizontal scanning, and the galvano mirror 54 for achieving a subsidiary or vertical scanning. Alternatively, the invention may be embodied in a form that the scanning subsystem 50 achieves both the principal and the subsidiary scanning by the use of a common optical element formed as a mirror. This form would contribute to an easy reduction of the corresponding image display apparatus 1, 2, in the total number of components thereof and in size thereof.

Still further, in the first and the second embodiment, the angle modifying subsystem 60 is adapted to reflect at the angle modifying mirror 61 the light beam emitted from the scanning subsystem 50, into the light-beam guiding subsystem 70. Alternatively, the angle modifying subsystem 60, given that it is still located to have an optical conjugate relationship with the pupil P, may be disposed at any position different from that in the first and the second embodiment. For example, the present invention may be embodied in a form that the angle modifying subsystem 60 is disposed at a position permitting the angle modifying subsystem 60 to receive the light beam from the polygon mirror 51, and to reflect the received light beam at the angle modifying mirror 61 into the galvano mirror 54.

Additionally, the invention is embodied in the first embodiment such that a desired display position of a virtual image is designated by the use of the position setting switch 84 of the control panel 80. Alternatively, the present invention may be embodied in a form that a device to enter a desired display position of a virtual image in numerical values (e.g., numerical values representing a distance from the pupil P, a direction relative to the pupil P, etc.), such as input keys is used for designating the desired display position.

In addition, the invention is embodied in the first and the second embodiment so as to use the Cartesian coordinate system the origin of which corresponds to the rotation center of the eye ball of the left eye EL for calculating or determining various parameters by the execution of the aforementioned image display program. Alternatively, the present invention may be embodied so as to calculate or determine various parameters by the use of a Cartesian coordinate system the origin of which corresponds to the position of the pupil P, based on the fact that the position of the angle modifying mirror 61 of the angle modifying subsystem 60 and the position of the pupil P (the position corresponding to the pupil P) have an optical conjugate relationship therebetween.

Third Embodiment

There will be next described a third embodiment of the present invention. Since the most of the elements used in the third embodiment correspond to those of the first embodiment, the corresponding elements will be identified by referring to the same reference numerals or titles, instead of explaining the corresponding elements in detail, while only the distinctive elements of the third embodiment will be explained in detail.

In the first embodiment, the angle modifying subsystem 60 is constructed to have both the angle modifying mirror 61 and the second relay optical system 68. Instead, in the present embodiment, the angle modifying subsystem 60 is constructed to use an optical element formed as a mirror in common with the scanning subsystem 50.

Figure 11:
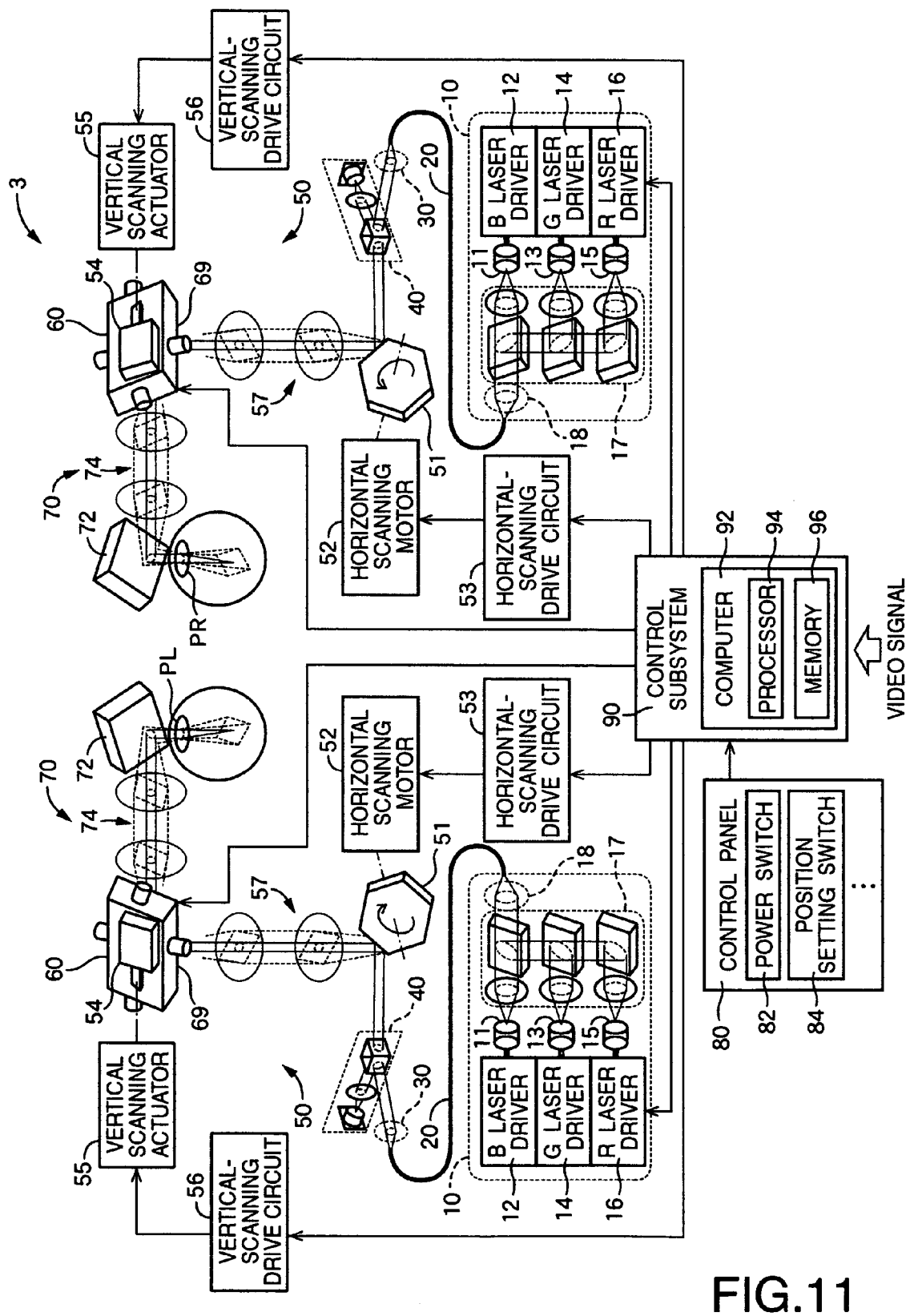
FIG. 11 is a schematic view illustrating an image display apparatus according to a third embodiment of the invention.

Referring to FIG. 11, an image display apparatus 3 constructed according to the present embodiment is illustrated as with FIG. 1. In the image display apparatus 3, the vertically modifying mechanism 62 and the horizontally modifying mechanism 66 of the angle modifying subsystem 60 are constructed to incline, instead of the angle modifying mirror 61, the reflective surface of the galvano mirror 54 vertically and horizontally, resulting in an integral construction of the angle modifying subsystem 60 and the galvano mirror 54 of the scanning subsystem 50.

Therefore, the present embodiment, because of a capability of the galvano mirror 54 to be functioned also as the angle modifying mirror 61, allows a removal of not only the angle modifying mirror 61 but also the second optical system 68 from the first embodiment.

Accordingly, the present embodiment provides an easy reduction in the total number of components of the image display apparatus 3, and eventually in size of the image display apparatus 3.

Fourth Embodiment

There will be next described a fourth embodiment of the present invention. Since the most of the elements used in the fourth embodiment correspond to those of the second embodiment, the corresponding elements will be identified by referring to the same reference numerals or titles, instead of explaining the corresponding elements in detail, while only the distinctive elements of the fourth embodiment will be explained in detail.

The second embodiment is constructed such that the computer 92 returns to the step S552, once it has been determined in the step S620 indicated in FIG. 8 that the input of the video signal is still continued.

On the other hand, in the present embodiment, a convergence-point changing switch (not shown) is provided with the control panel 80 of the image display apparatus 2, for permitting the viewer to operate the convergence-point changing switch to a change in the actual convergence point of the viewer's both eyes ER, EL.

Figure 12:
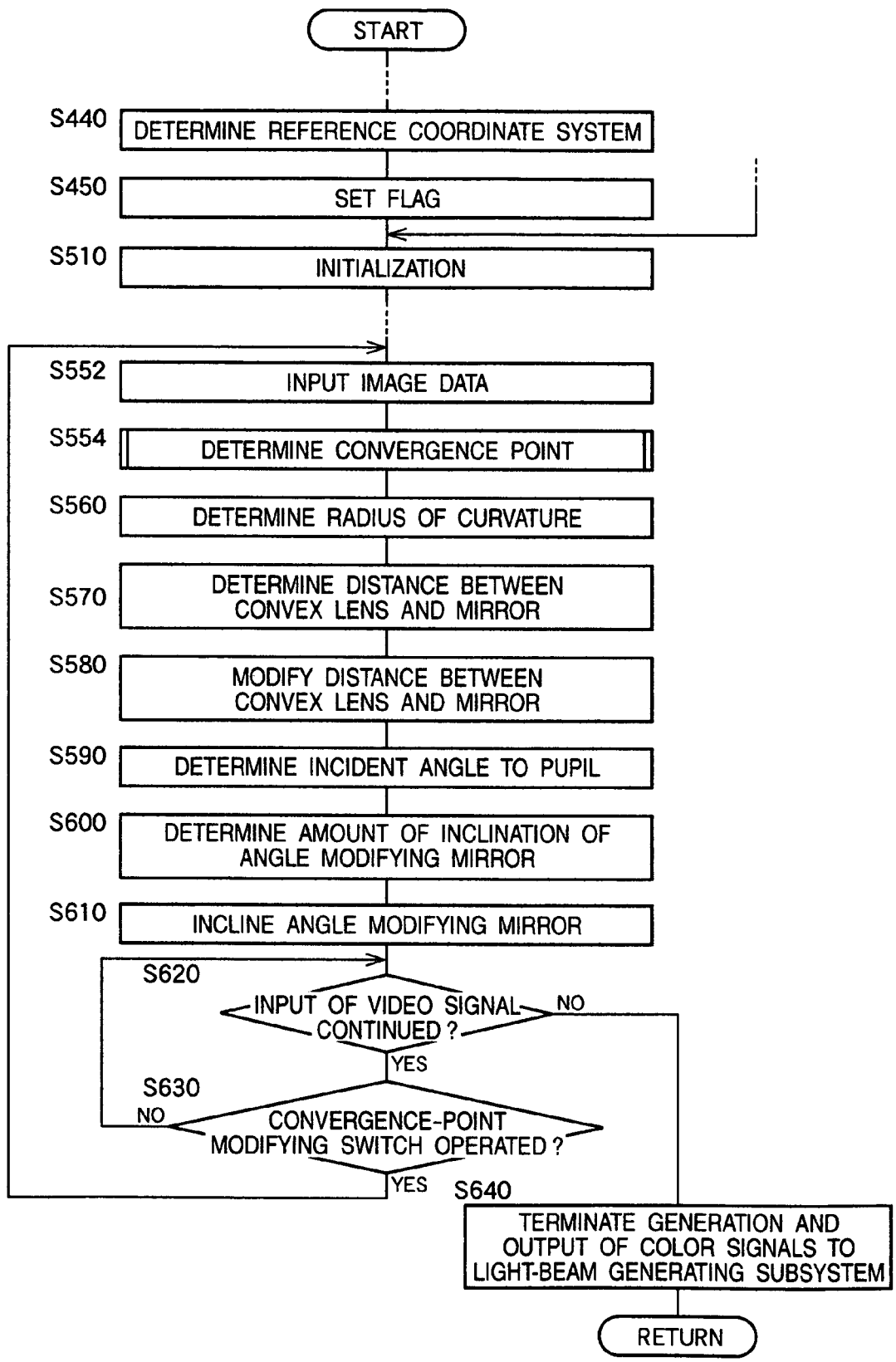
FIG. 12 is a flow chart conceptually illustrating an image display program used in an image display apparatus according to a fourth embodiment of the invention.

Referring to FIG. 12, an image display program according to the present embodiment is conceptually illustrated in a flow chart. The image display program, having the steps corresponding to those of the image display program according to the second embodiment, will be explained in detail only in regard to the distinctive steps thereof, while the image display program according to the present embodiment will be explained briefly in regard to the corresponding steps thereof by citing the identical numerals.

In the image display program according to the present embodiment, the steps S410 through S620 and S640 are implemented like in the first embodiment. However, unlike in the first embodiment in which the computer 92 returns to the step S552 immediately after the determination of the step S620 becomes affirmative "YES" since the input of the video signal has been continued, the image display program according to the present embodiment is executed such that the computer 92 determines in a step S630 whether or not the above-mentioned convergence-point changing switch has been operated by the viewer after an occurrence of the affirmative determination of the step S620.

If the convergence-point changing switch has not been operated, the determination of the step S630 becomes negative "NO", and in turn, the computer 92 returns to the step S620. Thereafter, as long as the input of the video signal is continued, both the generation of the color signals based on the input video signal and the output of the color signals to the light-beam generating subsystem 10 are continued.

To the contrary, if the convergence-point changing switch has been operated, the determination of the step S630 becomes affirmative "YES", and then the computer 92 returns to the step S552. Thereafter, it is repeated that the radius of curvature and the pupil incident angle are determined, and that the determined radius of curvature and/or the determined pupil incident angle are modified where necessary.

Fifth Embodiment

There will be next described a fifth embodiment of the present invention which differs from the above-described four embodiments in that a change in the direction of the display position of a virtual image relative to the viewer results from a modification of the angle of the mirror located in front of the viewer's pupil P.

Figure 13:
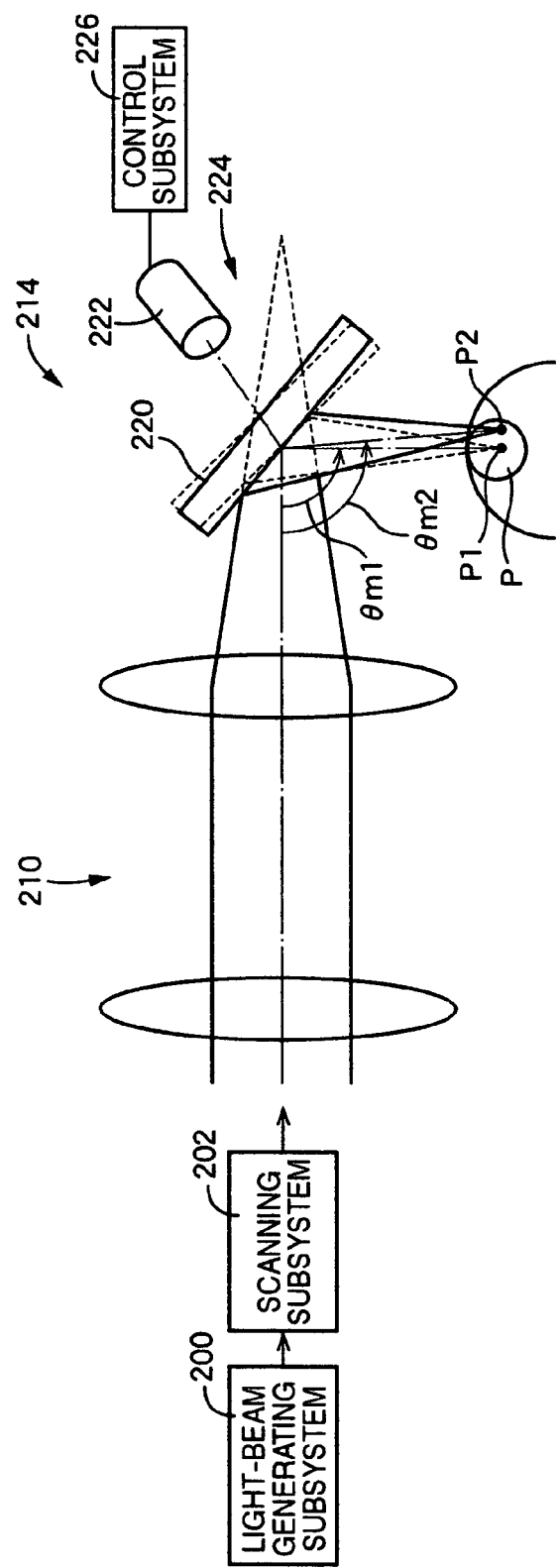
FIG. 13 is an optical ray diagram illustrating an image display apparatus according to a fifth embodiment of the invention.

In FIG. 13, the essential part of an image display apparatus constructed according to the present embodiment is illustrated in an optical ray diagram, while the remaining part thereof is briefly illustrated in a block diagram. The present embodiment includes a light-beam generating subsystem 200 and a scanning subsystem 202. The light-beam generating subsystem 200 bears the fundamental structure in common with the light-beam generating subsystem 10, and the scanning subsystem 202 bears the fundamental structure in common with the scanning subsystem 50. The scanning subsystem 202 scans the light beam emitted from the light-beam generating subsystem 200 in two dimensions, namely, horizontally and vertically.

As shown in FIG. 13, the light beam emitted from the scanning subsystem 202 is directed to an angle modifying subsystem 214 by means of a light-beam guiding subsystem 210. The angle modifying subsystem 214 is equipped with a mirror 220 in front of the pupil P.

The mirror 220 is rotatably supported at a frame (not shown) of the angle modifying subsystem 214. Specifically, the mirror 220 is supported so as to permit both the rotation about a horizontal axis and the rotation about a vertical axis, centered at the center position of the mirror 220 intersecting the center line (shown in a dash-dotted line in FIG. 13) of the scanning angle of the light beam emitted from the light-beam guiding subsystem 210.

For achieving the two rotations, the mirror 220 is connected with a driving device 224 including a drive source in the form of a motor 222. The driving device 224 is controlled by a control subsystem 226 having the same fundamental construction as the aforementioned control subsystem 90.

In FIG. 13, the angle between the center line of the scanning angle of the light beam entering the mirror 220 and the center line of the scanning angle of the light beam emitted from the mirror 220 is denoted by "θm1" for a first angular position shown in a broken line, while is denoted by "θm2" for a second angular position shown in a solid line. In the example indicated in FIG. 13, a change from the angle θm1 to θm2 corresponds to a modification of the pupil incident angle, which modification involves a change in the direction of the display position of a virtual image relative to the viewer.

Sixth Embodiment

There will be next described a sixth embodiment of the present invention. While the present embodiment is different from the fifth embodiment in the locus of motion of the mirror 220 for changing the display position of a virtual image, most of the elements used in the present embodiment correspond to those of the fifth embodiment. Therefore, the corresponding elements will be identified by referring to the same reference numerals or titles, instead of explaining the corresponding elements in detail, while only the distinctive elements of the sixth embodiment will be explained in detail.

Figure 14:
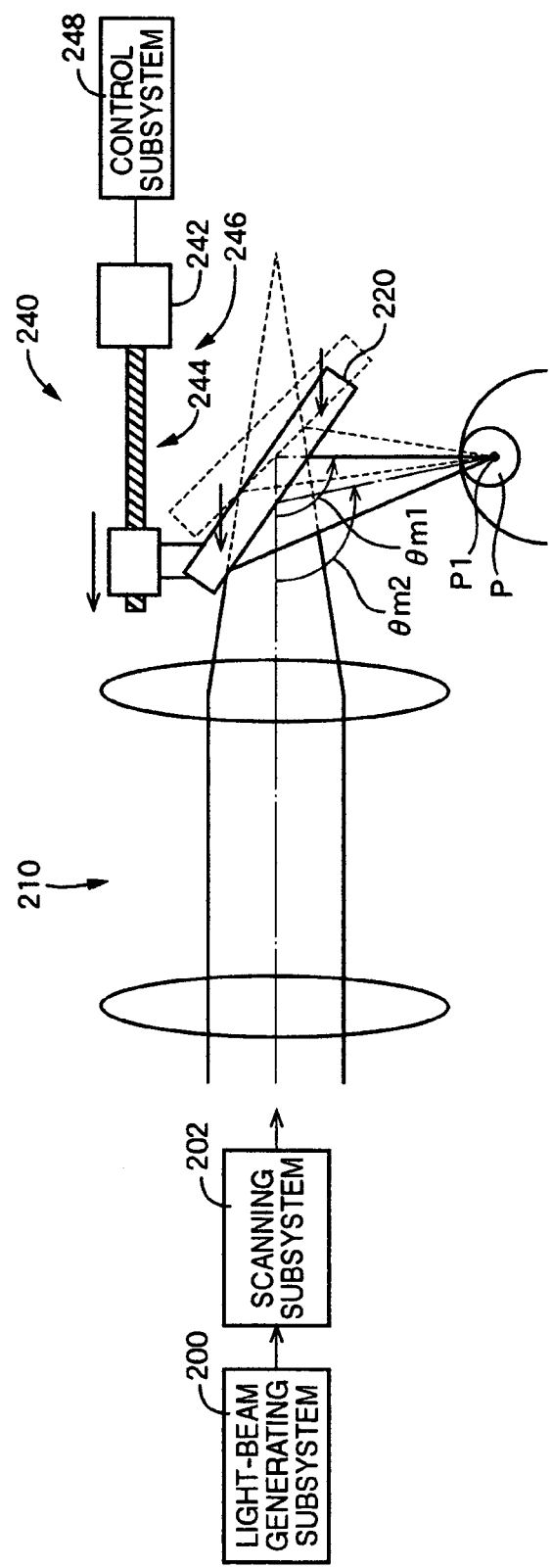
FIG. 14 is an optical ray diagram illustrating an image display apparatus according to a sixth embodiment of the invention.

As shown in FIG. 14, in the present embodiment, the light beam emitted from the scanning subsystem 202 is directed to an angle modifying subsystem 240 by means of the light-beam guiding subsystem 210. The angle modifying subsystem 240 is equipped with the mirror 220.

The mirror 220 is supported to a frame (not shown) of the angle modifying subsystem 240 so as to permit a motion for changing the angle between the mirror 220 and the light beam emitted from the light-beam guiding subsystem 210. Specifically, the mirror 220 is supported to be moved along the locus permitting the light beam reflected at the mirror 220 and then entering the pupil P to be focused or converged in the pupil P at on the same position P1, irrespective of a change in the angle between mirror 220 and the light beam emitted from the light-beam guiding subsystem 210. The mirror 220 involves a combined motion of both the rotation of the mirror 220 about the center position thereof and the translation of the mirror 220.

Therefore, in the present embodiment, unlike in the fifth embodiment, the center position of the mirror 220 is moved along the optical path of the light beam emitted from the light-beam guiding subsystem 210 during the rotation of the mirror 220.

To provide the above motion, the mirror 220 is attached to a driving device 246 including both a motor 242 serving as a driving source and a motion converting mechanism 244 for converting the rotation of a shaft of the motor 242 into the above combined motion.

The motion converting mechanism 244 is constructed to include a first portion permitting the rotation of the mirror 220 and a second portion permitting the translation of the mirror 220, as shown in FIG. 14 only for the second portion. The second portion is constructed to principally have a ball screw for converting the rotation of the shaft of the motor 242 into a linear motion. In addition, the above drive device 246 is controlled by a control subsystem 248 having the fundamental construction similar to that of the control subsystem 90.

In FIG. 14, the angle between the center line of the scanning angle of the light beam entering the mirror 220 and the center line of the scanning angle of light beam emitted from the mirror 220 is denoted by "θm1" for a first angular position shown in a broken line, while is denoted by "θm2" for a second angular position shown in a solid line. In the example shown in FIG. 14, a modification from the angle θm1 to θm2 corresponds to a modification of the aforementioned pupil incident angle which involves a change in the direction of the display position of a virtual image relative to the viewer.

As evident from the above, in the present embodiment, the light-beam generating subsystem 200 constitutes one example of the "light beam generator" set forth in the above mode (1), the scanning subsystem 202 constitutes one example of the "scanning device" set forth in the same mode, the light-beam guiding subsystem 210 constitutes one example of the "guiding device" set forth in the same mode, and the angle modifying subsystem 240 constitutes one example of the "angle modifying device" set forth in the same mode.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. An apparatus for introducing a light beam into a pupil of an eye of a viewer, to thereby project an image onto a retina of the eye, the apparatus comprising:
   a light beam generator for generating and outputting a light beam corresponding to the image;
   a scanning device for scanning the light beam output by the light beam generator;
   a guiding device for guiding the light beam scanned by the scanning device toward the pupil; and
   an angle modifying device for modifying a pupil incident angle at which a center line of a scanning angle through which the light beam is scanned by the scanning device enters the pupil, such that the center line passes through the pupil at a fixed position, irrespective of a change in the pupil incident angle.

2. The apparatus according to claim 1, wherein the angle modifying device is disposed at a position within a path extending from the scanning device to the guiding device, the position having an optical conjugate relationship with a position of the pupil.

3. An apparatus for introducing a light beam into a pupil of an eye of a viewer, to thereby project an image onto a retina of the eye, the apparatus comprising:
   a light beam generator for generating and outputting a light beam corresponding to the image;
   a scanning device for scanning the light beam output by the light beam generator;
   a guiding device for guiding the light beam scanned by the scanning device toward the pupil; and
   an angle modifying device for modifying a pupil incident angle at which a center line of a scanning angle through which the light beam is scanned by the scanning device enters the pupil, wherein the angle modifying device includes:
   a first modifier for modifying the pupil incident angle with respect to a first modifying direction; and
   a second modifier for modifying the pupil incident angle with respect to a second modifying direction intersecting the first modifying direction.

4. The apparatus according to claim 1, wherein the scanning device includes:
   a first scanner for scanning the light beam in a first scanning direction;
   a second scanner for scanning the light beam scanned by the first scanner in a second direction intersecting the first scanning direction; and a relay optical system for introducing the light beam from the first scanner to the second scanner, such that the first scanner and the second scanner have an optical conjugate relationship therebetween.

5. The apparatus according to claim 4, wherein the angle modifying device and the second scanner have an optical conjugate relationship therebetween.

6. The apparatus according to claim 1, wherein the guiding device includes:
a mirror arranged in front of the pupil; and
a relay optical system for introducing the light beam scanned by the scanning device into the mirror, such that an exit position at which the light beam exits from the scanning device and a position of the pupil have an optical conjugate relationship therebetween.

7. The apparatus according to claim 1, wherein the angle modifying device includes, a mirror arranged at a position having an optical conjugate relationship with a position of the pupil, and the apparatus further comprising a relay optical system for introducing the light beam scanned by the scanning device into the mirror, and wherein an exit position at which the light beam exits from the scanning device and a position of the mirror have an optical conjugate relationship therebetween.

8. The apparatus according to claim 1, wherein the angle modifying device modifies the pupil incident angle using an optical element common to the angle modifying device and the scanning device.

9. The apparatus according to claim 1, wherein the scanning device includes:
a first scanner for scanning the light beam in a first scanning direction; and
a second scanner for scanning the light beam in a second scanning direction intersecting the first scanning direction at a lower speed than the first scanner scans, and wherein the angle modifying device modifies the pupil incident angle using an optical element common to the angle modifying device and the second scanner.

10. An apparatus for introducing a first light beam into a first pupil of a first eye of a viewer and for introducing a second light beam into a second pupil of a second eye of the viewer, to thereby project an image onto each of a retina of the first eye and a retina of the second eye, the apparatus comprising:
a light beam generator for generating and outputting a first light beam and a second light beam corresponding to the image;
a first scanning device for scanning the first light beam output by the light beam generator;
a first guiding device for guiding the first light beam scanned by the first scanning device toward the first pupil;
a first angle modifying device for modifying a first pupil incident angle at which a first center line of a first scanning angle through which the first light beam is scanned by the first scanning device enters the first pupil;
a second guiding device for guiding the second light beam scanned by the second scanning device toward the second pupil of the second eye of the viewer;
a second angle modifying device for modifying a second pupil incident angle at which a second center line of a second scanning angle through which the second light beam is scanned by the second scanning device enters the second pupil;
a setting device for setting a display position at which the image is displayed in a form of a virtual image in front of the first pupil and the second pupil of the eyes, in response to an externally input command; and
a controller for controlling the first angle modifying device and the second angle modifying device, such that first and second extended center lines intersect each other at a set display position, wherein the first and second extended center lines are defined by extending back the first center line of the first light beam entering the first pupil from the first guiding device; and by extending the second center line of the second light beam entering the second pupil from the second guiding device, respectively.

11. The apparatus according to claim 10, wherein the setting device includes:
a sight-line sensor for detecting sight lines of the first eye and the second eye of the viewer; and
means for setting the display position to a position at which the sight lines detected by the sight-line sensor intersect each other.

12. The apparatus according to claim 10, wherein the setting device is constituted to set the display position of the image to any desired position in response to manipulation of the viewer.

13. The apparatus according to claim 10, further comprising:
a first wave-front-curvature modulator for modulating a first wave front curvature of the first light beam leaving the light beam generator and entering the first scanning device;
a second scanning wave-front-curvatur modulator for modulating a second wave front curvature of the second light beam leaving the light beam generator and entering the second scanning device; and
a commanding device for providing a command to the first wave-front-curvature modulator and the second wave-front-curvature modulator to attain a first value of the first wave front curvature in accordance with a distance from a distance from a position of the first pupil to the display position set by the setting device, and to attain a second value of the second wave front curvature in accordance with a distance from a position of the second pupil to the display position set by the setting device.

14. The apparatus according to claim 11, further comprising:
a first wave-front-curvature modulator for modulating a first wave-front-curvature of the first light beam leaving the light beam generator and entering the first scanning device;
a second wave-front-curvature modulator for modulating a second wave front curvature of the second light beam leaving the light beam generator and entering the second scanning device; and
means for controlling the first wave-front-curvature modulator and the second wave-front-curvature modulator to attain a first value of the first wave front curvature in accordance with a distance from a position of the first pupil to a position at which the sight lines detected by the sight-line sensor intersect each other, and a second value of the second wave front curvature in accordance with a distance from a position of the second pupil to the position at which the sight lines detected by the sight line sensor intersect each other.

15. The apparatus according to claim 13, wherein:
the first wave-front-curvature modulator includes:
a first lens for converging the first light beam output by the light beam generator;

a first mirror for reflecting the first light beam converged by the first lens to the first scanning device again through the first lens; and a first distance modifier for modifying a first distance between the first lens and the first mirror, to thereby change the first wave front curvature of the first light beam, and the second wave-front-curvature moderator includes:

a second lens for converging the second light beam output by the light beam generator;

a second mirror for reflecting the second light beam converged by the second lens to the second scanning device again through the second lens; and a second distance modifier for modifying a second distance between the second lens and the second mirror, to thereby change the second wave front curvature of the second light beam.

16. The apparatus according to claim 14, wherein:

the first wave-front-curvature modifier includes:

a first lens for converging the first light beam output by the light beam generator;

a first mirror for reflecting the first light beam converged by the first lens to the first scanning device again through the first lens; and a first distance modifier for modifying a first distance between the first lens and the first mirror, to thereby change the first wave front curvature of the light beam, and the second wave-front-curvature modulator includes:

a second lens for converging the second light beam output by the light beam generator;

a second mirror for reflecting the second light beam converged by the second lens to the second scanning device again through the second lens; and a second distance modifier for modifying a second distance between the second lens and the second mirror, to thereby change the second wave front curvature of the second light beam.

17. An apparatus for introducing a light beam into a pupil of an eye of a viewer, to thereby project an image onto a retina of the eye, the apparatus comprising:

a light beam generator for generating and outputting a light beam corresponding to the image;

a scanning device for scanning the light beam output by the light beam generator, including:

a first scanner for scanning the light beam in a first scanning direction; and a second scanner for scanning the light beam scanned by the first scanner in a second scanning direction intersecting the first scanning direction;

a guiding device for guiding the light beam scanned by the scanning device toward the pupil; and an angle modifying device for modifying a pupil incident angle at which a center line of a scanning angle through which the light beam is scanned by the scanning device enters the pupil, such that the center line passes through the pupil at a fixed position, irrespective of a change in the pupil incident angle, the angle modifyig device including a mirror for receiving the light beam scanned by the scanning device, wherein the first and the second scanner have an optical conjugate relationship therebetween, wherein the second scanner and the mirror have an optical conjugate relationship therebetween, and wherein the mirror and a position of the pupil have an optical conjugate relationship therebetween.

18. The apparatus according to claim 17, wherein the angle modifying device modifies the pupil incident angle using an optical element common to the angle modifying device and the scanning device.

* * * * *